(12) United States Patent
Badet-Denisot et al.

(10) Patent No.: US 7,625,734 B2
(45) Date of Patent: Dec. 1, 2009

(54) GLUTAMINE:FRUCTOSE-6-PHOSPHATE AMIDOTRANSFERASE (GFAT) COMPRISING AN INTERNAL PURIFICATION MARKER AND USE THEREOF FOR THE SCREENING OF COMPOUNDS

(75) Inventors: Marie-Ange Juliette Etiennette Badet-Denisot, Forges-les-Bains (FR); Barnard François Badet, Forges-les-Bains (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 326 days.

(21) Appl. No.: 10/563,572

(22) PCT Filed: Jul. 8, 2004

(86) PCT No.: PCT/FR2004/001800

§ 371 (c)(1),
(2), (4) Date: May 25, 2006

(87) PCT Pub. No.: WO2005/005628

PCT Pub. Date: Jan. 20, 2005

(65) Prior Publication Data
US 2006/0239989 A1 Oct. 26, 2006

(30) Foreign Application Priority Data
Jul. 8, 2003 (FR) .................................. 03 08350

(51) Int. Cl.
*C12N 9/10* (2006.01)
*C12N 9/00* (2006.01)
*C12N 1/20* (2006.01)
*C12N 15/00* (2006.01)
*A61K 38/00* (2006.01)
*C07H 21/04* (2006.01)

(52) U.S. Cl. ...................... 435/193; 424/94.5; 435/183; 435/252.3; 435/320.1; 536/23.2

(58) Field of Classification Search ....................... None
See application file for complete search history.

(56) References Cited

U.S. PATENT DOCUMENTS
5,710,248 A 1/1998 Grose

FOREIGN PATENT DOCUMENTS
WO    WO 93/21330    10/1993
WO    WO 97/07132    2/1997
WO    WO 02/090535   11/2002

OTHER PUBLICATIONS
Chang et al. J Biol Chem. Jul. 21, 2000;275(29):21981-7.*
Ferguson et al. Protein Sci. Jul. 1998;7(7):1636-8.*
Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner*—Christian L Fronda
(74) *Attorney, Agent, or Firm*—Young & Thompson

(57) ABSTRACT

The invention relates to a protein with enzymatic activity, comprising a GFAT sequence and at least one sequence of a purification marker, the sequence for the purification marker being inserted between two consecutive amino acids of the GFAT sequence.

7 Claims, 1 Drawing Sheet

Figure 1:
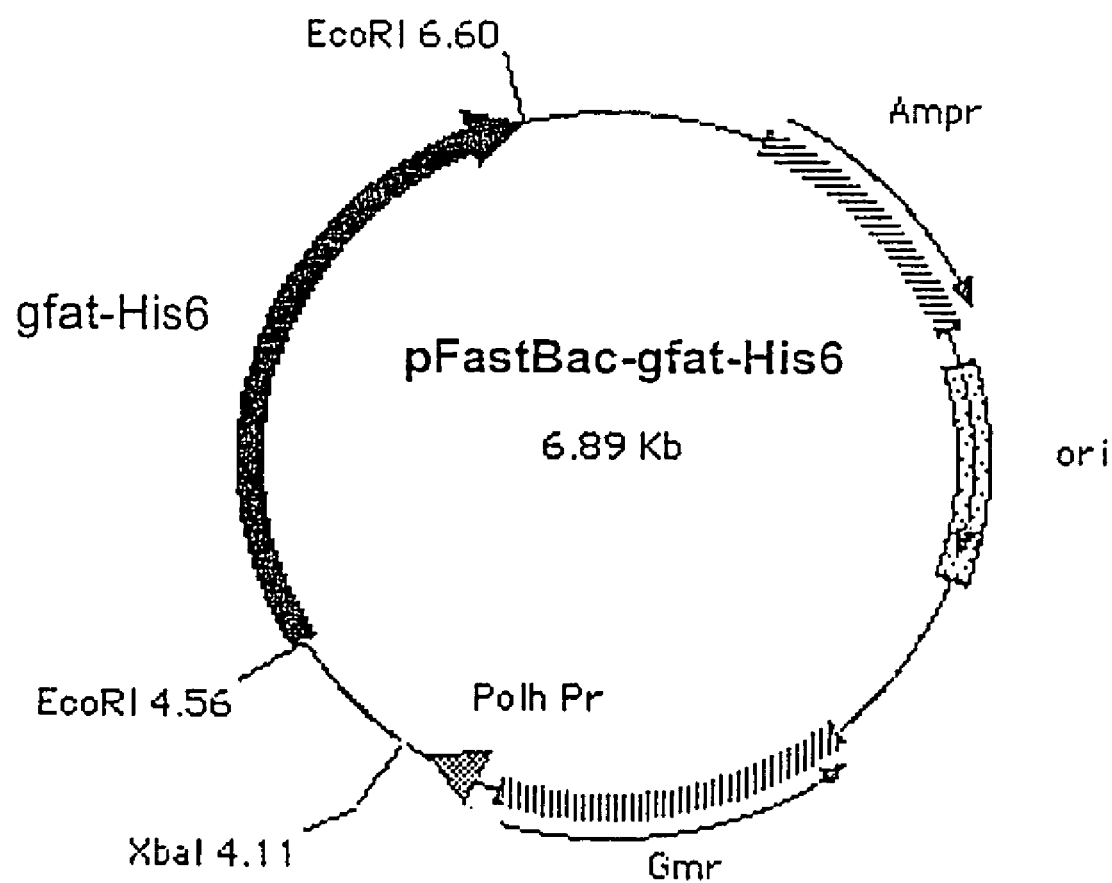

SEQUENCE LISTING

```
<160> NUMBER OF SEQ ID NOS: 19

<210> SEQ ID NO 1
<211> LENGTH: 2046
<212> TYPE: DNA
<213> ORGANISM: Homo sapiens
<220> FEATURE:
<221> NAME/KEY: CDS
<222> LOCATION: (1)..(2046)
<223> OTHER INFORMATION:
<220> FEATURE:
<221> NAME/KEY: misc_feature
<222> LOCATION: (170)..(170)
<223> OTHER INFORMATION: t ou c

<400> SEQUENCE: 1 atg tgt ggt ata ttt gct tac tta aac tac cat gtt cct cga acg aga      48
Met Cys Gly Ile Phe Ala Tyr Leu Asn Tyr His Val Pro Arg Thr Arg
1               5                   10                  15 cga gaa atc ctg gag acc cta atc aaa ggc ctt cag aga ctg gag tac      96
Arg Glu Ile Leu Glu Thr Leu Ile Lys Gly Leu Gln Arg Leu Glu Tyr
                20                  25                  30 aga gga tat gat tct gct ggt gtg gga ttt gat gga ggc aat gat aaa     144
Arg Gly Tyr Asp Ser Ala Gly Val Gly Phe Asp Gly Gly Asn Asp Lys
            35                  40                  45 gat tgg gaa gcc aat gcc tgc aaa anc cag ctt att aag aag aaa gga     192
Asp Trp Glu Ala Asn Ala Cys Lys Xaa Gln Leu Ile Lys Lys Lys Gly
        50                  55                  60 aaa gtt aag gca ctg gat gaa gaa gtt cac aag caa caa gat atg gat     240
Lys Val Lys Ala Leu Asp Glu Glu Val His Lys Gln Gln Asp Met Asp
65                  70                  75                  80 ttg gat ata gaa ttt gat gta cac ctt gga ata gct cat acc cgt tgg     288
Leu Asp Ile Glu Phe Asp Val His Leu Gly Ile Ala His Thr Arg Trp
                85                  90                  95 gca aca cat gga gaa ccc agt cct gtc aat agc cac ccc cag cgc tct     336
Ala Thr His Gly Glu Pro Ser Pro Val Asn Ser His Pro Gln Arg Ser
                100                 105                 110 gat aaa aat aat gaa ttt atc gtt att cac aat gga atc atc acc aac     384
Asp Lys Asn Asn Glu Phe Ile Val Ile His Asn Gly Ile Ile Thr Asn
            115                 120                 125
```

-continued

```
tac aaa gac ttg aaa aag ttt ttg gaa agc aaa ggc tat gac ttc gaa        432
Tyr Lys Asp Leu Lys Lys Phe Leu Glu Ser Lys Gly Tyr Asp Phe Glu
    130             135                 140 tct gaa aca gac aca gag aca att gcc aag ctc gtt aag tat atg tat        480
Ser Glu Thr Asp Thr Glu Thr Ile Ala Lys Leu Val Lys Tyr Met Tyr
145                 150                 155                 160 gac aat cgg gaa agt caa gat acc agc ttt act acc ttg gtg gag aga        528
Asp Asn Arg Glu Ser Gln Asp Thr Ser Phe Thr Thr Leu Val Glu Arg
                165                 170                 175 gtt atc caa caa ttg gaa ggt gct ttt gca ctt gtg ttt aaa agt gtt        576
Val Ile Gln Gln Leu Glu Gly Ala Phe Ala Leu Val Phe Lys Ser Val
            180                 185                 190 cat ttt ccc ggg caa gca gtt ggc aca agg cga ggt agc cct ctg ttg        624
His Phe Pro Gly Gln Ala Val Gly Thr Arg Arg Gly Ser Pro Leu Leu
        195                 200                 205 att ggt gta cgg agt gaa cat aaa ctt tct act gat cac att cct ata        672
Ile Gly Val Arg Ser Glu His Lys Leu Ser Thr Asp His Ile Pro Ile
    210                 215                 220 ctc tac aga aca ggc aaa gac aag aaa gga agc tgc aat ctc tct cgt        720
Leu Tyr Arg Thr Gly Lys Asp Lys Lys Gly Ser Cys Asn Leu Ser Arg
225                 230                 235                 240 gtg gac agc aca acc tgc ctt ttc ccg gtg gaa gaa aaa gca gtg gag        768
Val Asp Ser Thr Thr Cys Leu Phe Pro Val Glu Glu Lys Ala Val Glu
                245                 250                 255 tat tac ttt gct tct gat gca agt gct gtc ata gaa cac acc aat cgc        816
Tyr Tyr Phe Ala Ser Asp Ala Ser Ala Val Ile Glu His Thr Asn Arg
            260                 265                 270 gtc atc ttt ctg gaa gat gat gat gtt gca gca gta gtg gat gga cgt        864
Val Ile Phe Leu Glu Asp Asp Asp Val Ala Ala Val Val Asp Gly Arg
        275                 280                 285 ctt tct atc cat cga att aaa cga act gca gga gat cac ccc gga cga        912
Leu Ser Ile His Arg Ile Lys Arg Thr Ala Gly Asp His Pro Gly Arg
    290                 295                 300 gct gtg caa aca ctc cag atg gaa ctc cag cag atc atg aag ggc aac        960
Ala Val Gln Thr Leu Gln Met Glu Leu Gln Gln Ile Met Lys Gly Asn
305                 310                 315                 320 ttc agt tca ttt atg cag aag gaa ata ttt gag cag cca gag tct gtc       1008
Phe Ser Ser Phe Met Gln Lys Glu Ile Phe Glu Gln Pro Glu Ser Val
                325                 330                 335 gtg aac aca atg aga gga aga gtc aac ttt gat gac tat act gtg aat       1056
Val Asn Thr Met Arg Gly Arg Val Asn Phe Asp Asp Tyr Thr Val Asn
            340                 345                 350 ttg ggt ggt ttg aag gat cac ata aag gag atc cag aga tgc cgg cgt       1104
Leu Gly Gly Leu Lys Asp His Ile Lys Glu Ile Gln Arg Cys Arg Arg
        355                 360                 365 ttg att ctt att gct tgt gga aca agt tac cat gct ggt gta gca aca       1152
Leu Ile Leu Ile Ala Cys Gly Thr Ser Tyr His Ala Gly Val Ala Thr
    370                 375                 380 cgt caa gtt ctt gag gag ctg act gag ttg cct gtg atg gtg gaa cta       1200
Arg Gln Val Leu Glu Glu Leu Thr Glu Leu Pro Val Met Val Glu Leu
385                 390                 395                 400 gca agt gac ttc ctg gac aga aac aca cca gtc ttt cga gat gat gtt       1248
Ala Ser Asp Phe Leu Asp Arg Asn Thr Pro Val Phe Arg Asp Asp Val
                405                 410                 415 tgc ttt ttc ctt agt caa tca ggt gag aca gca gat act ttg atg ggt       1296
Cys Phe Phe Leu Ser Gln Ser Gly Glu Thr Ala Asp Thr Leu Met Gly
            420                 425                 430 ctt cgt tac tgt aag gag aga gga gct tta act gtg ggg atc aca aac       1344
Leu Arg Tyr Cys Lys Glu Arg Gly Ala Leu Thr Val Gly Ile Thr Asn
        435                 440                 445
```

```
aca gtt ggc agt tcc ata tca cgg gag aca gat tgt gga gtt cat att    1392
Thr Val Gly Ser Ser Ile Ser Arg Glu Thr Asp Cys Gly Val His Ile
    450                 455                 460 aat gct ggt cct gag att ggt gtg gcc agt aca aag gct tat acc agc    1440
Asn Ala Gly Pro Glu Ile Gly Val Ala Ser Thr Lys Ala Tyr Thr Ser
465                 470                 475                 480 cag ttt gta tcc ctt gtg atg ttt gcc ctt atg atg tgt gat gat cgg    1488
Gln Phe Val Ser Leu Val Met Phe Ala Leu Met Met Cys Asp Asp Arg
            485                 490                 495 atc tcc atg caa gaa aga cgc aaa gag atc atg ctt gga ttg aaa cgg    1536
Ile Ser Met Gln Glu Arg Arg Lys Glu Ile Met Leu Gly Leu Lys Arg
        500                 505                 510 ctg cct gat ttg att aag gaa gta ctg agc atg gat gac gaa att cag    1584
Leu Pro Asp Leu Ile Lys Glu Val Leu Ser Met Asp Asp Glu Ile Gln
    515                 520                 525 aaa cta gca aca gaa ctt tat cat cag aag tca gtt ctg ata atg gga    1632
Lys Leu Ala Thr Glu Leu Tyr His Gln Lys Ser Val Leu Ile Met Gly
530                 535                 540 cga ggc tat cat tat gct act tgt ctt gaa ggg gca ctg aaa atc aaa    1680
Arg Gly Tyr His Tyr Ala Thr Cys Leu Glu Gly Ala Leu Lys Ile Lys
545                 550                 555                 560 gaa att act tat atg cac tct gaa ggc atc ctt gct ggt gaa ttg aaa    1728
Glu Ile Thr Tyr Met His Ser Glu Gly Ile Leu Ala Gly Glu Leu Lys
            565                 570                 575 cat ggc cct ctg gct ttg gtg gat aaa ttg atg cct gtg atc atg atc    1776
His Gly Pro Leu Ala Leu Val Asp Lys Leu Met Pro Val Ile Met Ile
        580                 585                 590 atc atg aga gat cac act tat gcc aag tgt cag aat gct ctt cag caa    1824
Ile Met Arg Asp His Thr Tyr Ala Lys Cys Gln Asn Ala Leu Gln Gln
    595                 600                 605 gtg gtt gct cgg cag ggg cgg cct gtg gta att tgt gat aag gag gat    1872
Val Val Ala Arg Gln Gly Arg Pro Val Val Ile Cys Asp Lys Glu Asp
610                 615                 620 act gag acc att aag aac aca aaa aga acg atc aag gtg ccc cac tca    1920
Thr Glu Thr Ile Lys Asn Thr Lys Arg Thr Ile Lys Val Pro His Ser
625                 630                 635                 640 gtg gac tgc ttg cag ggc att ctc agc gtg atc cct tta cag ttg ctg    1968
Val Asp Cys Leu Gln Gly Ile Leu Ser Val Ile Pro Leu Gln Leu Leu
            645                 650                 655 gct ttc cac ctt gct gtg ctg aga ggc tat gat gtt gat ttc cca cgg    2016
Ala Phe His Leu Ala Val Leu Arg Gly Tyr Asp Val Asp Phe Pro Arg
        660                 665                 670 aat ctt gcc aaa tct gtg act gta gag tga                            2046
Asn Leu Ala Lys Ser Val Thr Val Glu
    675                 680

<210> SEQ ID NO 2
<211> LENGTH: 681
<212> TYPE: PRT
<213> ORGANISM: Homo sapiens
<220> FEATURE:
<221> NAME/KEY: misc_feature
<222> LOCATION: (57)..(57)
<223> OTHER INFORMATION: 'Xaa' in position 57 represents Thr or Ile.

<400> SEQUENCE: 2

Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30
```

-continued

```
Arg Gly Tyr Asp Ser Ala Gly Val Gly Phe Asp Gly Gly Asn Asp Lys
        35                  40                  45

Asp Trp Glu Ala Asn Ala Cys Lys Xaa Gln Leu Ile Lys Lys Lys Gly
50                  55                  60

Lys Val Lys Ala Leu Asp Glu Glu Val His Lys Gln Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser
                100                 105                 110

Asp Lys Asn Asn Glu Phe Ile Val Ile His Asn Gly Ile Ile Thr Asn
                115                 120                 125

Tyr Lys Asp Leu Lys Lys Phe Leu Glu Ser Lys Gly Tyr Asp Phe Glu
                130                 135                 140

Ser Glu Thr Asp Thr Glu Thr Ile Ala Lys Leu Val Lys Tyr Met Tyr
145                 150                 155                 160

Asp Asn Arg Glu Ser Gln Asp Thr Ser Phe Thr Thr Leu Val Glu Arg
                165                 170                 175

Val Ile Gln Gln Leu Glu Gly Ala Phe Ala Leu Val Phe Lys Ser Val
                180                 185                 190

His Phe Pro Gly Gln Ala Val Gly Thr Arg Arg Gly Ser Pro Leu Leu
                195                 200                 205

Ile Gly Val Arg Ser Glu His Lys Leu Ser Thr Asp His Ile Pro Ile
                210                 215                 220

Leu Tyr Arg Thr Gly Lys Asp Lys Lys Gly Ser Cys Asn Leu Ser Arg
225                 230                 235                 240

Val Asp Ser Thr Thr Cys Leu Phe Pro Val Glu Glu Lys Ala Val Glu
                245                 250                 255

Tyr Tyr Phe Ala Ser Asp Ala Ser Ala Val Ile Glu His Thr Asn Arg
                260                 265                 270

Val Ile Phe Leu Glu Asp Asp Val Ala Ala Val Asp Gly Arg
                275                 280                 285

Leu Ser Ile His Arg Ile Lys Arg Thr Ala Gly Asp His Pro Gly Arg
            290                 295                 300

Ala Val Gln Thr Leu Gln Met Glu Leu Gln Gln Ile Met Lys Gly Asn
305                 310                 315                 320

Phe Ser Ser Phe Met Gln Lys Glu Ile Phe Glu Gln Pro Glu Ser Val
                325                 330                 335

Val Asn Thr Met Arg Gly Arg Val Asn Phe Asp Asp Tyr Thr Val Asn
                340                 345                 350

Leu Gly Gly Leu Lys Asp His Ile Lys Glu Ile Gln Arg Cys Arg Arg
                355                 360                 365

Leu Ile Leu Ile Ala Cys Gly Thr Ser Tyr His Ala Gly Val Ala Thr
            370                 375                 380

Arg Gln Val Leu Glu Glu Leu Thr Glu Leu Pro Val Met Val Glu Leu
385                 390                 395                 400

Ala Ser Asp Phe Leu Asp Arg Asn Thr Pro Val Phe Arg Asp Asp Val
                405                 410                 415

Cys Phe Phe Leu Ser Gln Ser Gly Glu Thr Ala Asp Thr Leu Met Gly
                420                 425                 430

Leu Arg Tyr Cys Lys Glu Arg Gly Ala Leu Thr Val Gly Ile Thr Asn
            435                 440                 445

Thr Val Gly Ser Ser Ile Ser Arg Glu Thr Asp Cys Gly Val His Ile
```

-continued

```
                450                 455                 460
Asn Ala Gly Pro Glu Ile Gly Val Ala Ser Thr Lys Ala Tyr Thr Ser
465                 470                 475                 480

Gln Phe Val Ser Leu Val Met Phe Ala Leu Met Met Cys Asp Asp Arg
                485                 490                 495

Ile Ser Met Gln Glu Arg Arg Lys Glu Ile Met Leu Gly Leu Lys Arg
                500                 505                 510

Leu Pro Asp Leu Ile Lys Glu Val Leu Ser Met Asp Asp Glu Ile Gln
                515                 520                 525

Lys Leu Ala Thr Glu Leu Tyr His Gln Lys Ser Val Leu Ile Met Gly
530                 535                 540

Arg Gly Tyr His Tyr Ala Thr Cys Leu Glu Gly Ala Leu Lys Ile Lys
545                 550                 555                 560

Glu Ile Thr Tyr Met His Ser Glu Gly Ile Leu Ala Gly Glu Leu Lys
                565                 570                 575

His Gly Pro Leu Ala Leu Val Asp Lys Leu Met Pro Val Ile Met Ile
                580                 585                 590

Ile Met Arg Asp His Thr Tyr Ala Lys Cys Gln Asn Ala Leu Gln Gln
                595                 600                 605

Val Val Ala Arg Gln Gly Arg Pro Val Val Ile Cys Asp Lys Glu Asp
                610                 615                 620

Thr Glu Thr Ile Lys Asn Thr Lys Arg Thr Ile Lys Val Pro His Ser
625                 630                 635                 640

Val Asp Cys Leu Gln Gly Ile Leu Ser Val Ile Pro Leu Gln Leu Leu
                645                 650                 655

Ala Phe His Leu Ala Val Leu Arg Gly Tyr Asp Val Asp Phe Pro Arg
                660                 665                 670

Asn Leu Ala Lys Ser Val Thr Val Glu
                675                 680

<210> SEQ ID NO 3
<211> LENGTH: 2049
<212> TYPE: DNA
<213> ORGANISM: Homo sapiens
<220> FEATURE:
<221> NAME/KEY: CDS
<222> LOCATION: (1)..(2049)
<223> OTHER INFORMATION:

<400> SEQUENCE: 3 atg tgc gga atc ttt gcc tac atg aac tac aga gtc ccc cgg acg agg        48
Met Cys Gly Ile Phe Ala Tyr Met Asn Tyr Arg Val Pro Arg Thr Arg
1               5                   10                  15 aag gag atc ttc gaa acc ctc atc aag ggc ctg cag cgg ctg gag tac        96
Lys Glu Ile Phe Glu Thr Leu Ile Lys Gly Leu Gln Arg Leu Glu Tyr
            20                  25                  30 aga ggc tac gac tcg gca ggt gtg gcg atc gat ggg aat aat cac gaa       144
Arg Gly Tyr Asp Ser Ala Gly Val Ala Ile Asp Gly Asn Asn His Glu
        35                  40                  45 gtc aaa gaa aga cac att cag ctg gtc aag aaa agg ggg aaa gtc aag       192
Val Lys Glu Arg His Ile Gln Leu Val Lys Lys Arg Gly Lys Val Lys
    50                  55                  60 gct ctc gat gaa gaa ctt tac aaa caa gac agc atg gac tta aaa gtg       240
Ala Leu Asp Glu Glu Leu Tyr Lys Gln Asp Ser Met Asp Leu Lys Val
65                  70                  75                  80 gag ttt gag aca cac ttc ggc att gcc cac acg cgc tgg gcc acc cac       288
Glu Phe Glu Thr His Phe Gly Ile Ala His Thr Arg Trp Ala Thr His
                85                  90                  95
```

-continued

| | | |
|---|---|---|
| ggg gtc ccc agt gct gtc aac agc cac cct cag cgc tca gac aaa ggc<br>Gly Val Pro Ser Ala Val Asn Ser His Pro Gln Arg Ser Asp Lys Gly<br>          100                    105                  110 | | 336 |
| aac gaa ttt gtt gtc atc cac aat ggg atc atc aca aat tac aaa gat<br>Asn Glu Phe Val Val Ile His Asn Gly Ile Ile Thr Asn Tyr Lys Asp<br>115                    120                    125 | | 384 |
| ctg agg aaa ttt ctg gaa agc aaa ggc tac gag ttt gag tca gaa aca<br>Leu Arg Lys Phe Leu Glu Ser Lys Gly Tyr Glu Phe Glu Ser Glu Thr<br>    130                    135                  140 | | 432 |
| gat aca gag acc atc gcc aag ctg att aaa tat gtg ttc gac aac aga<br>Asp Thr Glu Thr Ile Ala Lys Leu Ile Lys Tyr Val Phe Asp Asn Arg<br>145                    150                    155                  160 | | 480 |
| gaa act gag gac att acg ttt tca acg ttg gtc gag aga gtc att cag<br>Glu Thr Glu Asp Ile Thr Phe Ser Thr Leu Val Glu Arg Val Ile Gln<br>                  165                    170                  175 | | 528 |
| cag ttg gaa ggt gca ttc gcg ctg gtt ttc aag agt gtc cac tac cca<br>Gln Leu Glu Gly Ala Phe Ala Leu Val Phe Lys Ser Val His Tyr Pro<br>            180                    185                  190 | | 576 |
| gga gaa gcc gtt gcc aca cgg aga ggc agc ccc ctc ctc atc gga gtc<br>Gly Glu Ala Val Ala Thr Arg Arg Gly Ser Pro Leu Leu Ile Gly Val<br>                  195                    200                  205 | | 624 |
| cgg agc aaa tac aag ctc tcc aca gaa cag atc cct atc tta tac agg<br>Arg Ser Lys Tyr Lys Leu Ser Thr Glu Gln Ile Pro Ile Leu Tyr Arg<br>210                    215                    220 | | 672 |
| acg tgc act ctg gag aat gtg aag aat atc tgt aag aca cgg atg aag<br>Thr Cys Thr Leu Glu Asn Val Lys Asn Ile Cys Lys Thr Arg Met Lys<br>225                    230                    235                  240 | | 720 |
| agg ctg gac agc tcc gcc tgc ctg cat gct gtg ggc gac aag gcc gtg<br>Arg Leu Asp Ser Ser Ala Cys Leu His Ala Val Gly Asp Lys Ala Val<br>                  245                    250                  255 | | 768 |
| gaa ttc ttc ttt gct tct gat gca agc gct atc ata gag cac acc aac<br>Glu Phe Phe Phe Ala Ser Asp Ala Ser Ala Ile Ile Glu His Thr Asn<br>            260                    265                  270 | | 816 |
| cgg gtc atc ttc ctg gag gac gat gac atc gcc gca gtg gct gat ggg<br>Arg Val Ile Phe Leu Glu Asp Asp Asp Ile Ala Ala Val Ala Asp Gly<br>275                    280                    285 | | 864 |
| aaa ctc tcc att cac cgg gtc aag cgc tcg gcc agt gat gac cca tct<br>Lys Leu Ser Ile His Arg Val Lys Arg Ser Ala Ser Asp Asp Pro Ser<br>    290                    295                  300 | | 912 |
| cga gcc atc cag acc ttg cag atg gaa ctg cag caa atc atg aaa ggt<br>Arg Ala Ile Gln Thr Leu Gln Met Glu Leu Gln Gln Ile Met Lys Gly<br>305                    310                    315                  320 | | 960 |
| aac ttc agt gcg ttt atg cag aag gag atc ttc gaa cag cca gaa tca<br>Asn Phe Ser Ala Phe Met Gln Lys Glu Ile Phe Glu Gln Pro Glu Ser<br>                  325                    330                  335 | | 1008 |
| gtt ttc aat act atg aga ggt cgg gtg aat ttt gaa acc aac aca gtg<br>Val Phe Asn Thr Met Arg Gly Arg Val Asn Phe Glu Thr Asn Thr Val<br>            340                    345                  350 | | 1056 |
| ctc ctg ggt ggc ttg aag gac cac ttg aag gag att cga cga tgc cga<br>Leu Leu Gly Gly Leu Lys Asp His Leu Lys Glu Ile Arg Arg Cys Arg<br>                  355                    360                  365 | | 1104 |
| cgg ctc atc gtg att ggc tgt gga acc agc tac cac gct gcc gtg gct<br>Arg Leu Ile Val Ile Gly Cys Gly Thr Ser Tyr His Ala Ala Val Ala<br>370                    375                    380 | | 1152 |
| acg cgg caa gtt ttg gag gaa ctg act gag ctt cct gtg atg gtt gaa<br>Thr Arg Gln Val Leu Glu Glu Leu Thr Glu Leu Pro Val Met Val Glu<br>385                    390                    395                  400 | | 1200 |
| ctt gct agt gat ttt ctg gac agg aac aca cct gtg ttc agg gat gac<br>Leu Ala Ser Asp Phe Leu Asp Arg Asn Thr Pro Val Phe Arg Asp Asp | | 1248 |

-continued

```
                  405                 410                 415
gtt tgc ttt ttc atc agc cag tca ggc gag acc gcg gac acc ctc ctg    1296
Val Cys Phe Phe Ile Ser Gln Ser Gly Glu Thr Ala Asp Thr Leu Leu
            420                 425                 430 gcg ctg cgc tac tgt aag gac cgc ggc gct ctc acc gtg ggc gtc acc    1344
Ala Leu Arg Tyr Cys Lys Asp Arg Gly Ala Leu Thr Val Gly Val Thr
        435                 440                 445 aac acc gtg ggc agc tcc atc tct cgc gag acc gac tgc ggc gtc cac    1392
Asn Thr Val Gly Ser Ser Ile Ser Arg Glu Thr Asp Cys Gly Val His
450                 455                 460 atc aac gca ggg ccg gag gtc ggc gtg gcc agc acc aag gct tat acc    1440
Ile Asn Ala Gly Pro Glu Val Gly Val Ala Ser Thr Lys Ala Tyr Thr
465                 470                 475                 480 agt cag ttc atc tct ctg gtg atg ttt ggt ttg atg atg tct gaa gac    1488
Ser Gln Phe Ile Ser Leu Val Met Phe Gly Leu Met Met Ser Glu Asp
                485                 490                 495 cga att tca cta caa aac agg agg caa gag atc atc cgt ggc ttg aga    1536
Arg Ile Ser Leu Gln Asn Arg Arg Gln Glu Ile Ile Arg Gly Leu Arg
            500                 505                 510 tct tta cct gag ctg atc aag gaa gtg ctg tct ctg gag gag aag atc    1584
Ser Leu Pro Glu Leu Ile Lys Glu Val Leu Ser Leu Glu Glu Lys Ile
        515                 520                 525 cac gac ttg gcc ctg gag ctc tac acg cag aga tcg ctg ctg gtg atg    1632
His Asp Leu Ala Leu Glu Leu Tyr Thr Gln Arg Ser Leu Leu Val Met
530                 535                 540 ggg cgg ggc tac aac tat gcc acc tgc ctg gaa gga gcc ctg aaa att    1680
Gly Arg Gly Tyr Asn Tyr Ala Thr Cys Leu Glu Gly Ala Leu Lys Ile
545                 550                 555                 560 aaa gag ata acc tac atg cac tca gaa ggc atc ctg gct ggg gag ctg    1728
Lys Glu Ile Thr Tyr Met His Ser Glu Gly Ile Leu Ala Gly Glu Leu
                565                 570                 575 aag cac ggg ccc ctg gca ctg att gac aag cag atg ccc gtc atc atg    1776
Lys His Gly Pro Leu Ala Leu Ile Asp Lys Gln Met Pro Val Ile Met
            580                 585                 590 gtc att atg aag gat cct tgc ttc gcc aaa tgc cag aac gcc ctg cag    1824
Val Ile Met Lys Asp Pro Cys Phe Ala Lys Cys Gln Asn Ala Leu Gln
        595                 600                 605 caa gtc acg gcc cgc cag ggt cgc ccc att ata ctg tgc tcc aag gac    1872
Gln Val Thr Ala Arg Gln Gly Arg Pro Ile Ile Leu Cys Ser Lys Asp
610                 615                 620 gat act gaa agt tcc aag ttt gcg tat aag aca atc gag ctg ccc cac    1920
Asp Thr Glu Ser Ser Lys Phe Ala Tyr Lys Thr Ile Glu Leu Pro His
625                 630                 635                 640 act gtg gac tgc ctc cag ggc atc ctg agc gtg att ccg ctg cag ctg    1968
Thr Val Asp Cys Leu Gln Gly Ile Leu Ser Val Ile Pro Leu Gln Leu
                645                 650                 655 ctg tcc ttc cac ctg gct gtt ctc cga gga tat gac gtt gac ttc ccc    2016
Leu Ser Phe His Leu Ala Val Leu Arg Gly Tyr Asp Val Asp Phe Pro
            660                 665                 670 aga aat ctg gcc aag tct gta act gtg gaa tga                        2049
Arg Asn Leu Ala Lys Ser Val Thr Val Glu
        675                 680
```

<210> SEQ ID NO 4
<211> LENGTH: 682
<212> TYPE: PRT
<213> ORGANISM: Homo sapiens

<400> SEQUENCE: 4

Met Cys Gly Ile Phe Ala Tyr Met Asn Tyr Arg Val Pro Arg Thr Arg

-continued

```
1               5                    10                   15
Lys Glu Ile Phe Glu Thr Leu Ile Lys Gly Leu Gln Arg Leu Glu Tyr
                20                  25                  30

Arg Gly Tyr Asp Ser Ala Gly Val Ala Ile Asp Gly Asn Asn His Glu
            35                  40                  45

Val Lys Glu Arg His Ile Gln Leu Val Lys Lys Arg Gly Lys Val Lys
        50                  55                  60

Ala Leu Asp Glu Glu Leu Tyr Lys Gln Asp Ser Met Asp Leu Lys Val
65                  70                  75                  80

Glu Phe Glu Thr His Phe Gly Ile Ala His Thr Arg Trp Ala Thr His
                85                  90                  95

Gly Val Pro Ser Ala Val Asn Ser His Pro Gln Arg Ser Asp Lys Gly
            100                 105                 110

Asn Glu Phe Val Val Ile His Asn Gly Ile Ile Thr Asn Tyr Lys Asp
        115                 120                 125

Leu Arg Lys Phe Leu Glu Ser Lys Gly Tyr Glu Phe Glu Ser Glu Thr
    130                 135                 140

Asp Thr Glu Thr Ile Ala Lys Leu Ile Lys Tyr Val Phe Asp Asn Arg
145                 150                 155                 160

Glu Thr Glu Asp Ile Thr Phe Ser Thr Leu Val Glu Arg Val Ile Gln
                165                 170                 175

Gln Leu Glu Gly Ala Phe Ala Leu Val Phe Lys Ser Val His Tyr Pro
            180                 185                 190

Gly Glu Ala Val Ala Thr Arg Arg Gly Ser Pro Leu Leu Ile Gly Val
        195                 200                 205

Arg Ser Lys Tyr Lys Leu Ser Thr Glu Gln Ile Pro Ile Leu Tyr Arg
    210                 215                 220

Thr Cys Thr Leu Glu Asn Val Lys Asn Ile Cys Lys Thr Arg Met Lys
225                 230                 235                 240

Arg Leu Asp Ser Ser Ala Cys Leu His Ala Val Gly Asp Lys Ala Val
                245                 250                 255

Glu Phe Phe Phe Ala Ser Asp Ala Ser Ala Ile Glu His Thr Asn
            260                 265                 270

Arg Val Ile Phe Leu Glu Asp Asp Ile Ala Ala Val Ala Asp Gly
        275                 280                 285

Lys Leu Ser Ile His Arg Val Lys Arg Ser Ala Ser Asp Pro Ser
    290                 295                 300

Arg Ala Ile Gln Thr Leu Gln Met Glu Leu Gln Ile Met Lys Gly
305                 310                 315                 320

Asn Phe Ser Ala Phe Met Gln Lys Glu Ile Phe Glu Gln Pro Glu Ser
                325                 330                 335

Val Phe Asn Thr Met Arg Gly Arg Val Asn Phe Glu Thr Asn Thr Val
            340                 345                 350

Leu Leu Gly Gly Leu Lys Asp His Leu Lys Glu Ile Arg Arg Cys Arg
        355                 360                 365

Arg Leu Ile Val Ile Gly Cys Gly Thr Ser Tyr His Ala Ala Val Ala
    370                 375                 380

Thr Arg Gln Val Leu Glu Glu Leu Thr Glu Leu Pro Val Met Val Glu
385                 390                 395                 400

Leu Ala Ser Asp Phe Leu Asp Arg Asn Thr Pro Val Phe Arg Asp Asp
                405                 410                 415

Val Cys Phe Phe Ile Ser Gln Ser Gly Glu Thr Ala Asp Thr Leu Leu
            420                 425                 430
```

```
Ala Leu Arg Tyr Cys Lys Asp Arg Gly Ala Leu Thr Val Gly Val Thr
            435                 440                 445

Asn Thr Val Gly Ser Ser Ile Ser Arg Glu Thr Asp Cys Gly Val His
        450                 455                 460

Ile Asn Ala Gly Pro Glu Val Gly Val Ala Ser Thr Lys Ala Tyr Thr
465                 470                 475                 480

Ser Gln Phe Ile Ser Leu Val Met Phe Gly Leu Met Met Ser Glu Asp
                485                 490                 495

Arg Ile Ser Leu Gln Asn Arg Gln Glu Ile Ile Arg Gly Leu Arg
            500                 505                 510

Ser Leu Pro Glu Leu Ile Lys Glu Val Leu Ser Leu Glu Glu Lys Ile
        515                 520                 525

His Asp Leu Ala Leu Glu Leu Tyr Thr Gln Arg Ser Leu Leu Val Met
    530                 535                 540

Gly Arg Gly Tyr Asn Tyr Ala Thr Cys Leu Glu Gly Ala Leu Lys Ile
545                 550                 555                 560

Lys Glu Ile Thr Tyr Met His Ser Glu Gly Ile Leu Ala Gly Glu Leu
                565                 570                 575

Lys His Gly Pro Leu Ala Leu Ile Asp Lys Gln Met Pro Val Ile Met
            580                 585                 590

Val Ile Met Lys Asp Pro Cys Phe Ala Lys Cys Gln Asn Ala Leu Gln
        595                 600                 605

Gln Val Thr Ala Arg Gln Gly Arg Pro Ile Ile Leu Cys Ser Lys Asp
    610                 615                 620

Asp Thr Glu Ser Ser Lys Phe Ala Tyr Lys Thr Ile Glu Leu Pro His
625                 630                 635                 640

Thr Val Asp Cys Leu Gln Gly Ile Leu Ser Val Ile Pro Leu Gln Leu
                645                 650                 655

Leu Ser Phe His Leu Ala Val Leu Arg Gly Tyr Asp Val Asp Phe Pro
            660                 665                 670

Arg Asn Leu Ala Lys Ser Val Thr Val Glu
        675                 680

<210> SEQ ID NO 5
<211> LENGTH: 2100
<212> TYPE: DNA
<213> ORGANISM: Homo sapiens
<220> FEATURE:
<221> NAME/KEY: CDS
<222> LOCATION: (1)..(2100)
<223> OTHER INFORMATION:
<220> FEATURE:
<221> NAME/KEY: misc_feature
<222> LOCATION: (170)..(170)
<223> OTHER INFORMATION: t or c

<400> SEQUENCE: 5 atg tgt ggt ata ttt gct tac tta aac tac cat gtt cct cga acg aga        48
Met Cys Gly Ile Phe Ala Tyr Leu Asn Tyr His Val Pro Arg Thr Arg
1               5                   10                  15 cga gaa atc ctg gag acc cta atc aaa ggc ctt cag aga ctg gag tac        96
Arg Glu Ile Leu Glu Thr Leu Ile Lys Gly Leu Gln Arg Leu Glu Tyr
            20                  25                  30 aga gga tat gat tct gct ggt gtg gga ttt gat gga ggc aat gat aaa       144
Arg Gly Tyr Asp Ser Ala Gly Val Gly Phe Asp Gly Gly Asn Asp Lys
        35                  40                  45 gat tgg gaa gcc aat gcc tgc aaa anc cag ctt att aag aag aaa gga       192
Asp Trp Glu Ala Asn Ala Cys Lys Xaa Gln Leu Ile Lys Lys Lys Gly
```

```
                50                      55                      60
aaa gtt aag gca ctg gat gaa gaa gtt cac aag caa caa gat atg gat    240
Lys Val Lys Ala Leu Asp Glu Glu Val His Lys Gln Gln Asp Met Asp
 65              70                      75                  80 ttg gat ata gaa ttt gat gta cac ctt gga ata gct cat acc cgt tgg    288
Leu Asp Ile Glu Phe Asp Val His Leu Gly Ile Ala His Thr Arg Trp
                     85                      90                  95 gca aca cat gga gaa ccc agt cct gtc aat agc cac ccc cag cgc tct    336
Ala Thr His Gly Glu Pro Ser Pro Val Asn Ser His Pro Gln Arg Ser
                100                     105                 110 gat aaa aat aat gaa ttt atc gtt att cac aat gga atc atc acc aac    384
Asp Lys Asn Asn Glu Phe Ile Val Ile His Asn Gly Ile Ile Thr Asn
            115                     120                 125 tac aaa gac ttg aaa aag ttt ttg gaa agc aaa ggc tat gac ttc gaa    432
Tyr Lys Asp Leu Lys Lys Phe Leu Glu Ser Lys Gly Tyr Asp Phe Glu
        130                     135                 140 tct gaa aca gac aca gag aca att gcc aag ctc gtt aag tat atg tat    480
Ser Glu Thr Asp Thr Glu Thr Ile Ala Lys Leu Val Lys Tyr Met Tyr
145                     150                     155                 160 gac aat cgg gaa agt caa gat acc agc ttt act acc ttg gtg gag aga    528
Asp Asn Arg Glu Ser Gln Asp Thr Ser Phe Thr Thr Leu Val Glu Arg
                165                     170                 175 gtt atc caa caa ttg gaa ggt gct ttt gca ctt gtg ttt aaa agt gtt    576
Val Ile Gln Gln Leu Glu Gly Ala Phe Ala Leu Val Phe Lys Ser Val
            180                     185                 190 cat ttt ccc ggg caa gca gtt ggc aca agg cga ggt agc cct ctg ttg    624
His Phe Pro Gly Gln Ala Val Gly Thr Arg Arg Gly Ser Pro Leu Leu
        195                     200                 205 att ggt gta cgg agt gaa cat aaa ctt tct act gat cac att cct ata    672
Ile Gly Val Arg Ser Glu His Lys Leu Ser Thr Asp His Ile Pro Ile
    210                     215                 220 ctc tac aga aca gct agg act cag att gga tca aaa ttc aca cgg tgg    720
Leu Tyr Arg Thr Ala Arg Thr Gln Ile Gly Ser Lys Phe Thr Arg Trp
225                     230                     235                 240 gga tca cag gga gaa aga ggc aaa gac aag aaa gga agc tgc aat ctc    768
Gly Ser Gln Gly Glu Arg Gly Lys Asp Lys Lys Gly Ser Cys Asn Leu
                245                     250                 255 tct cgt gtg gac agc aca acc tgc ctt ttc ccg gtg gaa gaa aaa gca    816
Ser Arg Val Asp Ser Thr Thr Cys Leu Phe Pro Val Glu Glu Lys Ala
            260                     265                 270 gtg gag tat tac ttt gct tct gat gca agt gct gtc ata gaa cac acc    864
Val Glu Tyr Tyr Phe Ala Ser Asp Ala Ser Ala Val Ile Glu His Thr
        275                     280                 285 aat cgc gtc atc ttt ctg gaa gat gat gat gtt gca gca gta gtg gat    912
Asn Arg Val Ile Phe Leu Glu Asp Asp Asp Val Ala Ala Val Val Asp
    290                     295                 300 gga cgt ctt tct atc cat cga att aaa cga act gca gga gat cac ccc    960
Gly Arg Leu Ser Ile His Arg Ile Lys Arg Thr Ala Gly Asp His Pro
305                     310                     315                 320 gga cga gct gtg caa aca ctc cag atg gaa ctc cag cag atc atg aag   1008
Gly Arg Ala Val Gln Thr Leu Gln Met Glu Leu Gln Gln Ile Met Lys
                325                     330                 335 ggc aac ttc agt tca ttt atg cag aag gaa ata ttt gag cag cca gag   1056
Gly Asn Phe Ser Ser Phe Met Gln Lys Glu Ile Phe Glu Gln Pro Glu
            340                     345                 350 tct gtc gtg aac aca atg aga gga aga gtc aac ttt gat gac tat act   1104
Ser Val Val Asn Thr Met Arg Gly Arg Val Asn Phe Asp Asp Tyr Thr
        355                     360                 365 gtg aat ttg ggt ggt ttg aag gat cac ata aag gag atc cag aga tgc   1152
```

```
                Val Asn Leu Gly Gly Leu Lys Asp His Ile Lys Glu Ile Gln Arg Cys
                    370             375             380 cgg cgt ttg att ctt att gct tgt gga aca agt tac cat gct ggt gta        1200
Arg Arg Leu Ile Leu Ile Ala Cys Gly Thr Ser Tyr His Ala Gly Val
385             390             395             400 gca aca cgt caa gtt ctt gag gag ctg act gag ttg cct gtg atg gtg        1248
Ala Thr Arg Gln Val Leu Glu Glu Leu Thr Glu Leu Pro Val Met Val
                405             410             415 gaa cta gca agt gac ttc ctg gac aga aac aca cca gtc ttt cga gat        1296
Glu Leu Ala Ser Asp Phe Leu Asp Arg Asn Thr Pro Val Phe Arg Asp
            420             425             430 gat gtt tgc ttt ttc ctt agt caa tca ggt gag aca gca gat act ttg        1344
Asp Val Cys Phe Phe Leu Ser Gln Ser Gly Glu Thr Ala Asp Thr Leu
        435             440             445 atg ggt ctt cgt tac tgt aag gag aga gga gct tta act gtg ggg atc        1392
Met Gly Leu Arg Tyr Cys Lys Glu Arg Gly Ala Leu Thr Val Gly Ile
    450             455             460 aca aac aca gtt ggc agt tcc ata tca cgg gag aca gat tgt gga gtt        1440
Thr Asn Thr Val Gly Ser Ser Ile Ser Arg Glu Thr Asp Cys Gly Val
465             470             475             480 cat att aat gct ggt cct gag att ggt gtg gcc agt aca aag gct tat        1488
His Ile Asn Ala Gly Pro Glu Ile Gly Val Ala Ser Thr Lys Ala Tyr
                485             490             495 acc agc cag ttt gta tcc ctt gtg atg ttt gcc ctt atg atg tgt gat        1536
Thr Ser Gln Phe Val Ser Leu Val Met Phe Ala Leu Met Met Cys Asp
                500             505             510 gat cgg atc tcc atg caa gaa aga cgc aaa gag atc atg ctt gga ttg        1584
Asp Arg Ile Ser Met Gln Glu Arg Arg Lys Glu Ile Met Leu Gly Leu
            515             520             525 aaa cgg ctg cct gat ttg att aag gaa gta ctg agc atg gat gac gaa        1632
Lys Arg Leu Pro Asp Leu Ile Lys Glu Val Leu Ser Met Asp Asp Glu
        530             535             540 att cag aaa cta gca aca gaa ctt tat cat cag aag tca gtt ctg ata        1680
Ile Gln Lys Leu Ala Thr Glu Leu Tyr His Gln Lys Ser Val Leu Ile
545             550             555             560 atg gga cga ggc tat cat tat gct act tgt ctt gaa ggg gca ctg aaa        1728
Met Gly Arg Gly Tyr His Tyr Ala Thr Cys Leu Glu Gly Ala Leu Lys
                565             570             575 atc aaa gaa att act tat atg cac tct gaa ggc atc ctt gct ggt gaa        1776
Ile Lys Glu Ile Thr Tyr Met His Ser Glu Gly Ile Leu Ala Gly Glu
                580             585             590 ttg aaa cat ggc cct ctg gct ttg gtg gat aaa ttg atg cct gtg atc        1824
Leu Lys His Gly Pro Leu Ala Leu Val Asp Lys Leu Met Pro Val Ile
            595             600             605 atg atc atc atg aga gat cac act tat gcc aag tgt cag aat gct ctt        1872
Met Ile Ile Met Arg Asp His Thr Tyr Ala Lys Cys Gln Asn Ala Leu
        610             615             620 cag caa gtg gtt gct cgg cag ggg cgg cct gtg gta att tgt gat aag        1920
Gln Gln Val Val Ala Arg Gln Gly Arg Pro Val Val Ile Cys Asp Lys
625             630             635             640 gag gat act gag acc att aag aac aca aaa aga acg atc aag gtg ccc        1968
Glu Asp Thr Glu Thr Ile Lys Asn Thr Lys Arg Thr Ile Lys Val Pro
                645             650             655 cac tca gtg gac tgc ttg cag ggc att ctc agc gtg atc cct tta cag        2016
His Ser Val Asp Cys Leu Gln Gly Ile Leu Ser Val Ile Pro Leu Gln
                660             665             670 ttg ctg gct ttc cac ctt gct gtg ctg aga ggc tat gat gtt gat ttc        2064
Leu Leu Ala Phe His Leu Ala Val Leu Arg Gly Tyr Asp Val Asp Phe
            675             680             685
```

```
cca cgg aat ctt gcc aaa tct gtg act gta gag tga                         2100
Pro Arg Asn Leu Ala Lys Ser Val Thr Val Glu
    690                 695
```

<210> SEQ ID NO 6
<211> LENGTH: 699
<212> TYPE: PRT
<213> ORGANISM: Homo sapiens
<220> FEATURE:
<221> NAME/KEY: misc_feature
<222> LOCATION: (57)..(57)
<223> OTHER INFORMATION: 'Xaa' in position 57 represents Thr or Ile

<400> SEQUENCE: 6

```
Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30

Arg Gly Tyr Asp Ser Ala Gly Val Gly Phe Asp Gly Gly Asn Asp Lys
        35                  40                  45

Asp Trp Glu Ala Asn Ala Cys Lys Xaa Gln Leu Ile Lys Lys Lys Gly
    50                  55                  60

Lys Val Lys Ala Leu Asp Glu Glu Val His Lys Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser
            100                 105                 110

Asp Lys Asn Asn Glu Phe Ile Val Ile His Asn Gly Ile Ile Thr Asn
        115                 120                 125

Tyr Lys Asp Leu Lys Lys Phe Leu Glu Ser Lys Gly Tyr Asp Phe Glu
    130                 135                 140

Ser Glu Thr Asp Thr Glu Thr Ile Ala Lys Leu Val Lys Tyr Met Tyr
145                 150                 155                 160

Asp Asn Arg Glu Ser Gln Asp Thr Ser Phe Thr Thr Leu Val Glu Arg
                165                 170                 175

Val Ile Gln Gln Leu Glu Gly Ala Phe Ala Leu Val Phe Lys Ser Val
            180                 185                 190

His Phe Pro Gly Gln Ala Val Gly Thr Arg Arg Gly Ser Pro Leu Leu
        195                 200                 205

Ile Gly Val Arg Ser Glu His Lys Leu Ser Thr Asp His Ile Pro Ile
    210                 215                 220

Leu Tyr Arg Thr Ala Arg Thr Gln Ile Gly Ser Lys Phe Thr Arg Trp
225                 230                 235                 240

Gly Ser Gln Gly Glu Arg Gly Lys Asp Lys Lys Gly Ser Cys Asn Leu
                245                 250                 255

Ser Arg Val Asp Ser Thr Thr Cys Leu Phe Pro Val Glu Glu Lys Ala
            260                 265                 270

Val Glu Tyr Tyr Phe Ala Ser Asp Ala Ser Ala Val Ile Glu His Thr
        275                 280                 285

Asn Arg Val Ile Phe Leu Glu Asp Asp Val Ala Ala Val Val Asp
    290                 295                 300

Gly Arg Leu Ser Ile His Arg Ile Lys Arg Thr Ala Gly Asp His Pro
305                 310                 315                 320

Gly Arg Ala Val Gln Thr Leu Gln Met Glu Leu Gln Gln Ile Met Lys
                325                 330                 335
```

```
Gly Asn Phe Ser Ser Phe Met Gln Lys Glu Ile Phe Glu Gln Pro Glu
                340                 345                 350

Ser Val Val Asn Thr Met Arg Gly Arg Val Asn Phe Asp Asp Tyr Thr
            355                 360                 365

Val Asn Leu Gly Gly Leu Lys Asp His Ile Lys Glu Ile Gln Arg Cys
        370                 375                 380

Arg Arg Leu Ile Leu Ile Ala Cys Gly Thr Ser Tyr His Ala Gly Val
385                 390                 395                 400

Ala Thr Arg Gln Val Leu Glu Glu Leu Thr Glu Leu Pro Val Met Val
                405                 410                 415

Glu Leu Ala Ser Asp Phe Leu Asp Arg Asn Thr Pro Val Phe Arg Asp
            420                 425                 430

Asp Val Cys Phe Phe Leu Ser Gln Ser Gly Glu Thr Ala Asp Thr Leu
        435                 440                 445

Met Gly Leu Arg Tyr Cys Lys Glu Arg Gly Ala Leu Thr Val Gly Ile
    450                 455                 460

Thr Asn Thr Val Gly Ser Ser Ile Ser Arg Glu Thr Asp Cys Gly Val
465                 470                 475                 480

His Ile Asn Ala Gly Pro Glu Ile Gly Val Ala Ser Thr Lys Ala Tyr
                485                 490                 495

Thr Ser Gln Phe Val Ser Leu Val Met Phe Ala Leu Met Met Cys Asp
            500                 505                 510

Asp Arg Ile Ser Met Gln Glu Arg Arg Lys Glu Ile Met Leu Gly Leu
        515                 520                 525

Lys Arg Leu Pro Asp Leu Ile Lys Glu Val Leu Ser Met Asp Asp Glu
    530                 535                 540

Ile Gln Lys Leu Ala Thr Glu Leu Tyr His Gln Lys Ser Val Leu Ile
545                 550                 555                 560

Met Gly Arg Gly Tyr His Tyr Ala Thr Cys Leu Glu Gly Ala Leu Lys
                565                 570                 575

Ile Lys Glu Ile Thr Tyr Met His Ser Glu Gly Ile Leu Ala Gly Glu
            580                 585                 590

Leu Lys His Gly Pro Leu Ala Leu Val Asp Lys Leu Met Pro Val Ile
        595                 600                 605

Met Ile Ile Met Arg Asp His Thr Tyr Ala Lys Cys Gln Asn Ala Leu
    610                 615                 620

Gln Gln Val Val Ala Arg Gln Gly Arg Pro Val Val Ile Cys Asp Lys
625                 630                 635                 640

Glu Asp Thr Glu Thr Ile Lys Asn Thr Lys Arg Thr Ile Lys Val Pro
                645                 650                 655

His Ser Val Asp Cys Leu Gln Gly Ile Leu Ser Val Ile Pro Leu Gln
            660                 665                 670

Leu Leu Ala Phe His Leu Ala Val Leu Arg Gly Tyr Asp Val Asp Phe
        675                 680                 685

Pro Arg Asn Leu Ala Lys Ser Val Thr Val Glu
    690                 695

<210> SEQ ID NO 7
<211> LENGTH: 2064
<212> TYPE: DNA
<213> ORGANISM: Artificial sequence
<220> FEATURE:
<223> OTHER INFORMATION: modified GFAT1 by an internal purification tag
<220> FEATURE:
<221> NAME/KEY: CDS
<222> LOCATION: (1)..(2064)
```

<220> FEATURE:
<221> NAME/KEY: misc_feature
<222> LOCATION: (170)..(170)
<223> OTHER INFORMATION: t or c

<400> SEQUENCE: 7

| | | | | | | | | | | | | | | | | |
|---|---|---|---|---|---|---|---|---|---|---|---|---|---|---|---|---|
| atg | tgt | ggt | ata | ttt | gct | tac | tta | aac | tac | cat | gtt | cct | cga | acg | aga | 48 |
| Met | Cys | Gly | Ile | Phe | Ala | Tyr | Leu | Asn | Tyr | His | Val | Pro | Arg | Thr | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cga | gaa | atc | ctg | gag | acc | cta | atc | aaa | ggc | ctt | cag | aga | ctg | gag | tac | 96 |
| Arg | Glu | Ile | Leu | Glu | Thr | Leu | Ile | Lys | Gly | Leu | Gln | Arg | Leu | Glu | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| aga | gga | tat | gat | tct | gct | ggt | gtg | gga | ttt | gat | gga | ggc | aat | gat | aaa | 144 |
| Arg | Gly | Tyr | Asp | Ser | Ala | Gly | Val | Gly | Phe | Asp | Gly | Gly | Asn | Asp | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| gat | tgg | gaa | gcc | aat | gcc | tgc | aaa | anc | cag | ctt | att | aag | aag | aaa | gga | 192 |
| Asp | Trp | Glu | Ala | Asn | Ala | Cys | Lys | Xaa | Gln | Leu | Ile | Lys | Lys | Lys | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| aaa | gtt | aag | gca | ctg | gat | gaa | gaa | gtt | cac | aag | caa | caa | gat | atg | gat | 240 |
| Lys | Val | Lys | Ala | Leu | Asp | Glu | Glu | Val | His | Lys | Gln | Gln | Asp | Met | Asp | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ttg | gat | ata | gaa | ttt | gat | gta | cac | ctt | gga | ata | gct | cat | acc | cgt | tgg | 288 |
| Leu | Asp | Ile | Glu | Phe | Asp | Val | His | Leu | Gly | Ile | Ala | His | Thr | Arg | Trp | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | aca | cat | gga | gaa | ccc | agt | cct | gtc | aat | agc | cac | ccc | cag | cgc | tct | 336 |
| Ala | Thr | His | Gly | Glu | Pro | Ser | Pro | Val | Asn | Ser | His | Pro | Gln | Arg | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| gat | aaa | aat | aat | gaa | ttt | atc | gtt | att | cac | aat | gga | atc | atc | acc | aac | 384 |
| Asp | Lys | Asn | Asn | Glu | Phe | Ile | Val | Ile | His | Asn | Gly | Ile | Ile | Thr | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| tac | aaa | gac | ttg | aaa | aag | ttt | ttg | gaa | agc | aaa | ggc | tat | gac | ttc | gaa | 432 |
| Tyr | Lys | Asp | Leu | Lys | Lys | Phe | Leu | Glu | Ser | Lys | Gly | Tyr | Asp | Phe | Glu | |
| 130 | | | | | 135 | | | | | 140 | | | | | | |

| | | | | | | | | | | | | | | | | |
|---|---|---|---|---|---|---|---|---|---|---|---|---|---|---|---|---|
| tct | gaa | aca | gac | aca | gag | aca | att | gcc | aag | ctc | gtt | aag | tat | atg | tat | 480 |
| Ser | Glu | Thr | Asp | Thr | Glu | Thr | Ile | Ala | Lys | Leu | Val | Lys | Tyr | Met | Tyr | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| gac | aat | cgg | gaa | agt | caa | gat | acc | agc | ttt | act | acc | ttg | gtg | gag | aga | 528 |
| Asp | Asn | Arg | Glu | Ser | Gln | Asp | Thr | Ser | Phe | Thr | Thr | Leu | Val | Glu | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| gtt | atc | caa | caa | ttg | gaa | ggt | gct | ttt | gca | ctt | gtg | ttt | aaa | agt | gtt | 576 |
| Val | Ile | Gln | Gln | Leu | Glu | Gly | Ala | Phe | Ala | Leu | Val | Phe | Lys | Ser | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| cat | ttt | ccc | ggg | caa | gca | gtt | ggc | aca | agg | cga | ggt | agc | cct | ctg | ttg | 624 |
| His | Phe | Pro | Gly | Gln | Ala | Val | Gly | Thr | Arg | Arg | Gly | Ser | Pro | Leu | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| att | ggt | gta | cgg | agt | gaa | cat | aaa | ctt | tct | act | gat | cac | att | cct | ata | 672 |
| Ile | Gly | Val | Arg | Ser | Glu | His | Lys | Leu | Ser | Thr | Asp | His | Ile | Pro | Ile | |
| 210 | | | | | 215 | | | | | 220 | | | | | | |

| | | | | | | | | | | | | | | | | |
|---|---|---|---|---|---|---|---|---|---|---|---|---|---|---|---|---|
| ctc | tac | aga | aca | ggc | aaa | gac | aag | aaa | gga | agc | tgc | aat | ctc | tct | cgt | 720 |
| Leu | Tyr | Arg | Thr | Gly | Lys | Asp | Lys | Lys | Gly | Ser | Cys | Asn | Leu | Ser | Arg | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| gtg | gac | agc | aca | acc | tgc | ctt | ttc | ccg | gtg | gaa | gaa | aaa | gca | gtg | gag | 768 |
| Val | Asp | Ser | Thr | Thr | Cys | Leu | Phe | Pro | Val | Glu | Glu | Lys | Ala | Val | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| tat | tac | ttt | gct | tct | gat | gca | agt | gct | gtc | ata | gaa | cac | acc | aat | cgc | 816 |
| Tyr | Tyr | Phe | Ala | Ser | Asp | Ala | Ser | Ala | Val | Ile | Glu | His | Thr | Asn | Arg | |
| | | | 260 | | | | | 265 | | | | | 270 | | | |

| | | | | | | | | | | | | | | | | |
|---|---|---|---|---|---|---|---|---|---|---|---|---|---|---|---|---|
| gtc | atc | ttt | ctg | gaa | gat | gat | gat | gtt | gca | gca | gta | gtg | gat | gga | cgt | 864 |
| Val | Ile | Phe | Leu | Glu | Asp | Asp | Asp | Val | Ala | Ala | Val | Val | Asp | Gly | Arg | |
| 275 | | | | | 280 | | | | | 285 | | | | | | |

```
                                          -continued ctt tct atc cat cga att aaa cga act gca gga cat cac cat cac cat      912
Leu Ser Ile His Arg Ile Lys Arg Thr Ala Gly His His His His His
    290                 295                 300 cac gat cac ccc gga cga gct gtg caa aca ctc cag atg gaa ctc cag      960
His Asp His Pro Gly Arg Ala Val Gln Thr Leu Gln Met Glu Leu Gln
305                 310                 315                 320 cag atc atg aag ggc aac ttc agt tca ttt atg cag aag gaa ata ttt     1008
Gln Ile Met Lys Gly Asn Phe Ser Ser Phe Met Gln Lys Glu Ile Phe
                325                 330                 335 gag cag cca gag tct gtc gtg aac aca atg aga gga aga gtc aac ttt     1056
Glu Gln Pro Glu Ser Val Val Asn Thr Met Arg Gly Arg Val Asn Phe
            340                 345                 350 gat gac tat act gtg aat ttg ggt ggt ttg aag gat cac ata aag gag     1104
Asp Asp Tyr Thr Val Asn Leu Gly Gly Leu Lys Asp His Ile Lys Glu
        355                 360                 365 atc cag aga tgc cgg cgt ttg att ctt att gct tgt gga aca agt tac     1152
Ile Gln Arg Cys Arg Arg Leu Ile Leu Ile Ala Cys Gly Thr Ser Tyr
    370                 375                 380 cat gct ggt gta gca aca cgt caa gtt ctt gag gag ctg act gag ttg     1200
His Ala Gly Val Ala Thr Arg Gln Val Leu Glu Glu Leu Thr Glu Leu
385                 390                 395                 400 cct gtg atg gtg gaa cta gca agt gac ttc ctg gac aga aac aca cca     1248
Pro Val Met Val Glu Leu Ala Ser Asp Phe Leu Asp Arg Asn Thr Pro
                405                 410                 415 gtc ttt cga gat gat gtt tgc ttc ttc ctt agt caa tca ggt gag aca     1296
Val Phe Arg Asp Asp Val Cys Phe Phe Leu Ser Gln Ser Gly Glu Thr
            420                 425                 430 gca gat act ttg atg ggt ctt cgt tac tgt aag gag aga gga gct tta     1344
Ala Asp Thr Leu Met Gly Leu Arg Tyr Cys Lys Glu Arg Gly Ala Leu
        435                 440                 445 act gtg ggg atc aca aac aca gtt ggc agt tcc ata tca cgg gag aca     1392
Thr Val Gly Ile Thr Asn Thr Val Gly Ser Ser Ile Ser Arg Glu Thr
    450                 455                 460 gat tgt gga gtt cat att aat gct ggt cct gag att ggt gtg gcc agt     1440
Asp Cys Gly Val His Ile Asn Ala Gly Pro Glu Ile Gly Val Ala Ser
465                 470                 475                 480 aca aag gct tat acc agc cag ttt gta tcc ctt gtg atg ttt gcc ctt     1488
Thr Lys Ala Tyr Thr Ser Gln Phe Val Ser Leu Val Met Phe Ala Leu
                485                 490                 495 atg atg tgt gat gat cgg atc tcc atg caa gaa aga cgc aaa gag atc     1536
Met Met Cys Asp Asp Arg Ile Ser Met Gln Glu Arg Arg Lys Glu Ile
            500                 505                 510 atg ctt gga ttg aaa cgg ctg cct gat ttg att aag gaa gta ctg agc     1584
Met Leu Gly Leu Lys Arg Leu Pro Asp Leu Ile Lys Glu Val Leu Ser
        515                 520                 525 atg gat gac gaa att cag aaa cta gca aca gaa ctt tat cat cag aag     1632
Met Asp Asp Glu Ile Gln Lys Leu Ala Thr Glu Leu Tyr His Gln Lys
    530                 535                 540 tca gtt ctg ata atg gga cga ggc tat cat tat gct act tgt ctt gaa     1680
Ser Val Leu Ile Met Gly Arg Gly Tyr His Tyr Ala Thr Cys Leu Glu
545                 550                 555                 560 ggg gca ctg aaa atc aaa gaa att act tat atg cac tct gaa ggc atc     1728
Gly Ala Leu Lys Ile Lys Glu Ile Thr Tyr Met His Ser Glu Gly Ile
                565                 570                 575 ctt gct ggt gaa ttg aaa cat ggc cct ctg gct ttg gtg gat aaa ttg     1776
Leu Ala Gly Glu Leu Lys His Gly Pro Leu Ala Leu Val Asp Lys Leu
            580                 585                 590 atg cct gtg atc atg atc atc atg aga gat cac act tat gcc aag tgt     1824
Met Pro Val Ile Met Ile Ile Met Arg Asp His Thr Tyr Ala Lys Cys
```

-continued

```
                      595                   600                   605
cag aat gct ctt cag caa gtg gtt gct cgg cag ggg cgg cct gtg gta        1872
Gln Asn Ala Leu Gln Gln Val Val Ala Arg Gln Gly Arg Pro Val Val
        610                   615                   620 att tgt gat aag gag gat act gag acc att aag aac aca aaa aga acg        1920
Ile Cys Asp Lys Glu Asp Thr Glu Thr Ile Lys Asn Thr Lys Arg Thr
625                   630                   635                   640 atc aag gtg ccc cac tca gtg gac tgc ttg cag ggc att ctc agc gtg        1968
Ile Lys Val Pro His Ser Val Asp Cys Leu Gln Gly Ile Leu Ser Val
                645                   650                   655 atc cct tta cag ttg ctg gct ttc cac ctt gct gtg ctg aga ggc tat        2016
Ile Pro Leu Gln Leu Leu Ala Phe His Leu Ala Val Leu Arg Gly Tyr
            660                   665                   670 gat gtt gat ttc cca cgg aat ctt gcc aaa tct gtg act gta gag tga        2064
Asp Val Asp Phe Pro Arg Asn Leu Ala Lys Ser Val Thr Val Glu
        675                   680                   685
```

<210> SEQ ID NO 8
<211> LENGTH: 687
<212> TYPE: PRT
<213> ORGANISM: Artificial sequence
<220> FEATURE:
<221> NAME/KEY: misc_feature
<222> LOCATION: (57)..(57)
<223> OTHER INFORMATION: 'Xaa' in position 57 represents Thr or Ile
<220> FEATURE:
<223> OTHER INFORMATION: modified GFAT1 by an internal purification tag

<400> SEQUENCE: 8

```
Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30

Arg Gly Tyr Asp Ser Ala Gly Val Gly Phe Asp Gly Gly Asn Asp Lys
        35                  40                  45

Asp Trp Glu Ala Asn Ala Cys Lys Xaa Gln Leu Ile Lys Lys Lys Gly
    50                  55                  60

Lys Val Lys Ala Leu Asp Glu Glu Val His Lys Gln Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser
            100                 105                 110

Asp Lys Asn Asn Glu Phe Ile Val Ile His Asn Gly Ile Ile Thr Asn
        115                 120                 125

Tyr Lys Asp Leu Lys Lys Phe Leu Glu Ser Lys Gly Tyr Asp Phe Glu
    130                 135                 140

Ser Glu Thr Asp Thr Glu Thr Ile Ala Lys Leu Val Lys Tyr Met Tyr
145                 150                 155                 160

Asp Asn Arg Glu Ser Gln Asp Thr Ser Phe Thr Thr Leu Val Glu Arg
                165                 170                 175

Val Ile Gln Gln Leu Glu Gly Ala Phe Ala Leu Val Phe Lys Ser Val
            180                 185                 190

His Phe Pro Gly Gln Ala Val Gly Thr Arg Arg Gly Ser Pro Leu Leu
        195                 200                 205

Ile Gly Val Arg Ser Glu His Lys Leu Ser Thr Asp His Ile Pro Ile
    210                 215                 220

Leu Tyr Arg Thr Gly Lys Asp Lys Lys Gly Ser Cys Asn Leu Ser Arg
```

-continued

```
            225                 230                 235                 240
Val Asp Ser Thr Thr Cys Leu Phe Pro Val Glu Glu Lys Ala Val Glu
                245                 250                 255

Tyr Tyr Phe Ala Ser Asp Ala Ser Ala Val Ile Glu His Thr Asn Arg
                260                 265                 270

Val Ile Phe Leu Glu Asp Asp Val Ala Ala Val Val Asp Gly Arg
                275                 280                 285

Leu Ser Ile His Arg Ile Lys Arg Thr Ala Gly His His His His
                290                 295                 300

His Asp His Pro Gly Arg Ala Val Gln Thr Leu Gln Met Glu Leu Gln
305                 310                 315                 320

Gln Ile Met Lys Gly Asn Phe Ser Ser Phe Met Gln Lys Glu Ile Phe
                325                 330                 335

Glu Gln Pro Glu Ser Val Val Asn Thr Met Arg Gly Arg Val Asn Phe
                340                 345                 350

Asp Asp Tyr Thr Val Asn Leu Gly Gly Leu Lys Asp His Ile Lys Glu
                355                 360                 365

Ile Gln Arg Cys Arg Arg Leu Ile Leu Ile Ala Cys Gly Thr Ser Tyr
                370                 375                 380

His Ala Gly Val Ala Thr Arg Gln Val Leu Glu Glu Leu Thr Glu Leu
385                 390                 395                 400

Pro Val Met Val Glu Leu Ala Ser Asp Phe Leu Asp Arg Asn Thr Pro
                405                 410                 415

Val Phe Arg Asp Asp Val Cys Phe Phe Leu Ser Gln Ser Gly Glu Thr
                420                 425                 430

Ala Asp Thr Leu Met Gly Leu Arg Tyr Cys Lys Glu Arg Gly Ala Leu
                435                 440                 445

Thr Val Gly Ile Thr Asn Thr Val Gly Ser Ser Ile Ser Arg Glu Thr
                450                 455                 460

Asp Cys Gly Val His Ile Asn Ala Gly Pro Glu Ile Gly Val Ala Ser
465                 470                 475                 480

Thr Lys Ala Tyr Thr Ser Gln Phe Val Ser Leu Val Met Phe Ala Leu
                485                 490                 495

Met Met Cys Asp Asp Arg Ile Ser Met Gln Glu Arg Arg Lys Glu Ile
                500                 505                 510

Met Leu Gly Leu Lys Arg Leu Pro Asp Leu Ile Lys Glu Val Leu Ser
                515                 520                 525

Met Asp Asp Glu Ile Gln Lys Leu Ala Thr Glu Leu Tyr His Gln Lys
                530                 535                 540

Ser Val Leu Ile Met Gly Arg Gly Tyr His Tyr Ala Thr Cys Leu Glu
545                 550                 555                 560

Gly Ala Leu Lys Ile Lys Glu Ile Thr Tyr Met His Ser Glu Gly Ile
                565                 570                 575

Leu Ala Gly Glu Leu Lys His Gly Pro Leu Ala Leu Val Asp Lys Leu
                580                 585                 590

Met Pro Val Ile Met Ile Met Arg Asp His Thr Tyr Ala Lys Cys
                595                 600                 605

Gln Asn Ala Leu Gln Gln Val Val Ala Arg Gln Gly Arg Pro Val Val
                610                 615                 620

Ile Cys Asp Lys Glu Asp Thr Glu Thr Ile Lys Asn Thr Lys Arg Thr
625                 630                 635                 640

Ile Lys Val Pro His Ser Val Asp Cys Leu Gln Gly Ile Leu Ser Val
                645                 650                 655
```

```
Ile Pro Leu Gln Leu Leu Ala Phe His Leu Ala Val Leu Arg Gly Tyr
            660                 665                 670

Asp Val Asp Phe Pro Arg Asn Leu Ala Lys Ser Val Thr Val Glu
        675                 680                 685

<210> SEQ ID NO 9
<211> LENGTH: 2067
<212> TYPE: DNA
<213> ORGANISM: Artificial sequence
<220> FEATURE:
<223> OTHER INFORMATION: modified GFAT2 by an internal purification tag
<220> FEATURE:
<221> NAME/KEY: CDS
<222> LOCATION: (1)..(2067)
<223> OTHER INFORMATION:

<400> SEQUENCE: 9 atg tgc gga atc ttt gcc tac atg aac tac aga gtc ccc cgg acg agg     48
Met Cys Gly Ile Phe Ala Tyr Met Asn Tyr Arg Val Pro Arg Thr Arg
1               5                   10                  15 aag gag atc ttc gaa acc ctc atc aag ggc ctg cag cgg ctg gag tac     96
Lys Glu Ile Phe Glu Thr Leu Ile Lys Gly Leu Gln Arg Leu Glu Tyr
            20                  25                  30 aga ggc tac gac tcg gca ggt gtg gcg atc gat ggg aat aat cac gaa    144
Arg Gly Tyr Asp Ser Ala Gly Val Ala Ile Asp Gly Asn Asn His Glu
        35                  40                  45 gtc aaa gaa aga cac att cag ctg gtc aag aaa agg ggg aaa gtc aag    192
Val Lys Glu Arg His Ile Gln Leu Val Lys Lys Arg Gly Lys Val Lys
    50                  55                  60 gct ctc gat gaa gaa ctt tac aaa caa gac agc atg gac tta aaa gtg    240
Ala Leu Asp Glu Glu Leu Tyr Lys Gln Asp Ser Met Asp Leu Lys Val
65                  70                  75                  80 gag ttt gag aca cac ttc ggc att gcc cac acg cgc tgg gcc acc cac    288
Glu Phe Glu Thr His Phe Gly Ile Ala His Thr Arg Trp Ala Thr His
                85                  90                  95 ggg gtc ccc agt gct gtc aac agc cac cct cag cgc tca gac aaa ggc    336
Gly Val Pro Ser Ala Val Asn Ser His Pro Gln Arg Ser Asp Lys Gly
            100                 105                 110 aac gaa ttt gtt gtc atc cac aat ggg atc atc aca aat tac aaa gat    384
Asn Glu Phe Val Val Ile His Asn Gly Ile Ile Thr Asn Tyr Lys Asp
        115                 120                 125 ctg agg aaa ttt ctg gaa agc aaa ggc tac gag ttt gag tca gaa aca    432
Leu Arg Lys Phe Leu Glu Ser Lys Gly Tyr Glu Phe Glu Ser Glu Thr
    130                 135                 140 gat aca gag acc atc gcc aag ctg att aaa tat gtg ttc gac aac aga    480
Asp Thr Glu Thr Ile Ala Lys Leu Ile Lys Tyr Val Phe Asp Asn Arg
145                 150                 155                 160 gaa act gag gac att acg ttt tca acg ttg gtc gag aga gtc att cag    528
Glu Thr Glu Asp Ile Thr Phe Ser Thr Leu Val Glu Arg Val Ile Gln
                165                 170                 175 cag ttg gaa ggt gca ttc gcg ctg gtt ttc aag agt gtc cac tac cca    576
Gln Leu Glu Gly Ala Phe Ala Leu Val Phe Lys Ser Val His Tyr Pro
            180                 185                 190 gga gaa gcc gtt gcc aca cgg aga ggc agc ccc ctc ctc atc gga gtc    624
Gly Glu Ala Val Ala Thr Arg Arg Gly Ser Pro Leu Leu Ile Gly Val
        195                 200                 205 cgg agc aaa tac aag ctc tcc aca gaa cag atc cct atc tta tac agg    672
Arg Ser Lys Tyr Lys Leu Ser Thr Glu Gln Ile Pro Ile Leu Tyr Arg
    210                 215                 220 acg tgc act ctg gag aat gtg aag aat atc tgt aag aca cgg atg aag    720
Thr Cys Thr Leu Glu Asn Val Lys Asn Ile Cys Lys Thr Arg Met Lys
```

-continued

```
              225                 230                 235                 240
agg ctg gac agc tcc gcc tgc ctg cat gct gtg ggc gac aag gcc gtg        768
Arg Leu Asp Ser Ser Ala Cys Leu His Ala Val Gly Asp Lys Ala Val
                245                 250                 255 gaa ttc ttc ttt gct tct gat gca agc gct atc ata gag cac acc aac        816
Glu Phe Phe Phe Ala Ser Asp Ala Ser Ala Ile Ile Glu His Thr Asn
            260                 265                 270 cgg gtc atc ttc ctg gag gac gat gac atc gcc gca gtg gct gat ggg        864
Arg Val Ile Phe Leu Glu Asp Asp Asp Ile Ala Ala Val Ala Asp Gly
        275                 280                 285 aaa ctc tcc att cac cgg gtc aag cgc tcg gcc agt cat cac cat cac        912
Lys Leu Ser Ile His Arg Val Lys Arg Ser Ala Ser His His His His
    290                 295                 300 cat cac gat gac cca tct cga gcc atc cag acc ttg cag atg gaa ctg        960
His His Asp Asp Pro Ser Arg Ala Ile Gln Thr Leu Gln Met Glu Leu
305                 310                 315                 320 cag caa atc atg aaa ggt aac ttc agt gcg ttt atg cag aag gag atc       1008
Gln Gln Ile Met Lys Gly Asn Phe Ser Ala Phe Met Gln Lys Glu Ile
                325                 330                 335 ttc gaa cag cca gaa tca gtt ttc aat act atg aga ggt cgg gtg aat       1056
Phe Glu Gln Pro Glu Ser Val Phe Asn Thr Met Arg Gly Arg Val Asn
            340                 345                 350 ttt gaa acc aac aca gtg ctc ctg ggt ggc ttg aag gac cac ttg aag       1104
Phe Glu Thr Asn Thr Val Leu Leu Gly Gly Leu Lys Asp His Leu Lys
        355                 360                 365 gag att cga cga tgc cga cgg ctc atc gtg att ggc tgt gga acc agc       1152
Glu Ile Arg Arg Cys Arg Arg Leu Ile Val Ile Gly Cys Gly Thr Ser
    370                 375                 380 tac cac gct gcc gtg gct acg cgg caa gtt ttg gag gaa ctg act gag       1200
Tyr His Ala Ala Val Ala Thr Arg Gln Val Leu Glu Glu Leu Thr Glu
385                 390                 395                 400 ctt cct gtg atg gtt gaa ctt gct agt gat ttt ctg gac agg aac aca       1248
Leu Pro Val Met Val Glu Leu Ala Ser Asp Phe Leu Asp Arg Asn Thr
                405                 410                 415 cct gtg ttc agg gat gac gtt tgc ttt ttc atc agc cag tca ggc gag       1296
Pro Val Phe Arg Asp Asp Val Cys Phe Phe Ile Ser Gln Ser Gly Glu
            420                 425                 430 acc gcg gac acc ctc ctg gcg ctg cgc tac tgt aag gac cgc ggc gct       1344
Thr Ala Asp Thr Leu Leu Ala Leu Arg Tyr Cys Lys Asp Arg Gly Ala
        435                 440                 445 ctc acc gtg ggc gtc acc aac acc gtg ggc agc tcc atc tct cgc gag       1392
Leu Thr Val Gly Val Thr Asn Thr Val Gly Ser Ser Ile Ser Arg Glu
    450                 455                 460 acc gac tgc ggc gtc cac atc aac gca ggg ccg gag gtc ggc gtg gcc       1440
Thr Asp Cys Gly Val His Ile Asn Ala Gly Pro Glu Val Gly Val Ala
465                 470                 475                 480 agc acc aag gct tat acc agt cag ttc atc tct ctg gtg atg ttt ggt       1488
Ser Thr Lys Ala Tyr Thr Ser Gln Phe Ile Ser Leu Val Met Phe Gly
                485                 490                 495 ttg atg atg tct gaa gac cga att tca cta caa aac agg agg caa gag       1536
Leu Met Met Ser Glu Asp Arg Ile Ser Leu Gln Asn Arg Arg Gln Glu
            500                 505                 510 atc atc cgt ggc ttg aga tct tta cct gag ctg atc aag gaa gtg ctg       1584
Ile Ile Arg Gly Leu Arg Ser Leu Pro Glu Leu Ile Lys Glu Val Leu
        515                 520                 525 tct ctg gag gag aag atc cac gac ttg gcc ctg gag ctc tac acg cag       1632
Ser Leu Glu Glu Lys Ile His Asp Leu Ala Leu Glu Leu Tyr Thr Gln
    530                 535                 540 aga tcg ctg ctg gtg atg ggg cgg ggc tac aac tat gcc acc tgc ctg       1680
```

```
                                    -continued

Arg Ser Leu Leu Val Met Gly Arg Gly Tyr Asn Tyr Ala Thr Cys Leu
545                 550                 555                 560 gaa gga gcc ctg aaa att aaa gag ata acc tac atg cac tca gaa ggc    1728
Glu Gly Ala Leu Lys Ile Lys Glu Ile Thr Tyr Met His Ser Glu Gly
                565                 570                 575 atc ctg gct ggg gag ctg aag cac ggg ccc ctg gca ctg att gac aag    1776
Ile Leu Ala Gly Glu Leu Lys His Gly Pro Leu Ala Leu Ile Asp Lys
            580                 585                 590 cag atg ccc gtc atc atg gtc att atg aag gat cct tgc ttc gcc aaa    1824
Gln Met Pro Val Ile Met Val Ile Met Lys Asp Pro Cys Phe Ala Lys
        595                 600                 605 tgc cag aac gcc ctg cag caa gtc acg gcc cgc cag ggt cgc ccc att    1872
Cys Gln Asn Ala Leu Gln Gln Val Thr Ala Arg Gln Gly Arg Pro Ile
    610                 615                 620 ata ctg tgc tcc aag gac gat act gaa agt tcc aag ttt gcg tat aag    1920
Ile Leu Cys Ser Lys Asp Asp Thr Glu Ser Ser Lys Phe Ala Tyr Lys
625                 630                 635                 640 aca atc gag ctg ccc cac act gtg gac tgc ctc cag ggc atc ctg agc    1968
Thr Ile Glu Leu Pro His Thr Val Asp Cys Leu Gln Gly Ile Leu Ser
                645                 650                 655 gtg att ccg ctg cag ctg ctg tcc ttc cac ctg gct gtt ctc cga gga    2016
Val Ile Pro Leu Gln Leu Leu Ser Phe His Leu Ala Val Leu Arg Gly
            660                 665                 670 tat gac gtt gac ttc ccc aga aat ctg gcc aag tct gta act gtg gaa    2064
Tyr Asp Val Asp Phe Pro Arg Asn Leu Ala Lys Ser Val Thr Val Glu
        675                 680                 685 tga                                                                2067

<210> SEQ ID NO 10
<211> LENGTH: 688
<212> TYPE: PRT
<213> ORGANISM: Artificial sequence
<220> FEATURE:
<223> OTHER INFORMATION: modified GFAT2 by an internal purification tag

<400> SEQUENCE: 10

Met Cys Gly Ile Phe Ala Tyr Met Asn Tyr Arg Val Pro Arg Thr Arg
1               5                   10                  15

Lys Glu Ile Phe Glu Thr Leu Ile Lys Gly Leu Gln Arg Leu Glu Tyr
                20                  25                  30

Arg Gly Tyr Asp Ser Ala Gly Val Ala Ile Asp Gly Asn Asn His Glu
            35                  40                  45

Val Lys Glu Arg His Ile Gln Leu Val Lys Lys Arg Gly Lys Val Lys
        50                  55                  60

Ala Leu Asp Glu Glu Leu Tyr Lys Gln Asp Ser Met Asp Leu Lys Val
65                  70                  75                  80

Glu Phe Glu Thr His Phe Gly Ile Ala His Thr Arg Trp Ala Thr His
                85                  90                  95

Gly Val Pro Ser Ala Val Asn Ser His Pro Gln Arg Ser Asp Lys Gly
            100                 105                 110

Asn Glu Phe Val Val Ile His Asn Gly Ile Ile Thr Asn Tyr Lys Asp
        115                 120                 125

Leu Arg Lys Phe Leu Glu Ser Lys Gly Tyr Glu Phe Glu Ser Glu Thr
    130                 135                 140

Asp Thr Glu Thr Ile Ala Lys Leu Ile Lys Tyr Val Phe Asp Asn Arg
145                 150                 155                 160

Glu Thr Glu Asp Ile Thr Phe Ser Thr Leu Val Glu Arg Val Ile Gln
                165                 170                 175
```

-continued

```
Gln Leu Glu Gly Ala Phe Ala Leu Val Phe Lys Ser Val His Tyr Pro
            180                 185                 190
Gly Glu Ala Val Ala Thr Arg Arg Gly Ser Pro Leu Leu Ile Gly Val
        195                 200                 205
Arg Ser Lys Tyr Lys Leu Ser Thr Glu Gln Ile Pro Ile Leu Tyr Arg
        210                 215                 220
Thr Cys Thr Leu Glu Asn Val Lys Asn Ile Cys Lys Thr Arg Met Lys
225                 230                 235                 240
Arg Leu Asp Ser Ser Ala Cys Leu His Ala Val Gly Asp Lys Ala Val
                245                 250                 255
Glu Phe Phe Phe Ala Ser Asp Ala Ser Ala Ile Ile Glu His Thr Asn
            260                 265                 270
Arg Val Ile Phe Leu Glu Asp Asp Ile Ala Ala Val Ala Asp Gly
        275                 280                 285
Lys Leu Ser Ile His Arg Val Lys Arg Ser Ala Ser His His His
        290                 295                 300
His His Asp Asp Pro Ser Arg Ala Ile Gln Thr Leu Gln Met Glu Leu
305                 310                 315                 320
Gln Gln Ile Met Lys Gly Asn Phe Ser Ala Phe Met Gln Lys Glu Ile
                325                 330                 335
Phe Glu Gln Pro Glu Ser Val Phe Asn Thr Met Arg Gly Arg Val Asn
            340                 345                 350
Phe Glu Thr Asn Thr Val Leu Leu Gly Gly Leu Lys Asp His Leu Lys
        355                 360                 365
Glu Ile Arg Arg Cys Arg Arg Leu Ile Val Ile Gly Cys Gly Thr Ser
    370                 375                 380
Tyr His Ala Ala Val Ala Thr Arg Gln Val Leu Glu Glu Leu Thr Glu
385                 390                 395                 400
Leu Pro Val Met Val Glu Leu Ala Ser Asp Phe Leu Asp Arg Asn Thr
                405                 410                 415
Pro Val Phe Arg Asp Asp Val Cys Phe Phe Ile Ser Gln Ser Gly Glu
            420                 425                 430
Thr Ala Asp Thr Leu Leu Ala Leu Arg Tyr Cys Lys Asp Arg Gly Ala
        435                 440                 445
Leu Thr Val Gly Val Thr Asn Thr Val Gly Ser Ser Ile Ser Arg Glu
        450                 455                 460
Thr Asp Cys Gly Val His Ile Asn Ala Gly Pro Glu Val Gly Val Ala
465                 470                 475                 480
Ser Thr Lys Ala Tyr Thr Ser Gln Phe Ile Ser Leu Val Met Phe Gly
                485                 490                 495
Leu Met Met Ser Glu Asp Arg Ile Ser Leu Gln Asn Arg Arg Gln Glu
            500                 505                 510
Ile Ile Arg Gly Leu Arg Ser Leu Pro Glu Leu Ile Lys Glu Val Leu
        515                 520                 525
Ser Leu Glu Glu Lys Ile His Asp Leu Ala Leu Glu Leu Tyr Thr Gln
    530                 535                 540
Arg Ser Leu Leu Val Met Gly Arg Gly Tyr Asn Tyr Ala Thr Cys Leu
545                 550                 555                 560
Glu Gly Ala Leu Lys Ile Lys Glu Ile Thr Tyr Met His Ser Glu Gly
                565                 570                 575
Ile Leu Ala Gly Glu Leu Lys His Gly Pro Leu Ala Leu Ile Asp Lys
            580                 585                 590
```

-continued

```
Gln Met Pro Val Ile Met Val Ile Met Lys Asp Pro Cys Phe Ala Lys
        595                 600                 605
Cys Gln Asn Ala Leu Gln Val Thr Ala Arg Gln Gly Arg Pro Ile
    610                 615                 620
Ile Leu Cys Ser Lys Asp Asp Thr Glu Ser Ser Lys Phe Ala Tyr Lys
625                 630                 635                 640
Thr Ile Glu Leu Pro His Thr Val Asp Cys Leu Gln Gly Ile Leu Ser
            645                 650                 655
Val Ile Pro Leu Gln Leu Leu Ser Phe His Leu Ala Val Leu Arg Gly
        660                 665                 670
Tyr Asp Val Asp Phe Pro Arg Asn Leu Ala Lys Ser Val Thr Val Glu
    675                 680                 685
```

<210> SEQ ID NO 11
<211> LENGTH: 2118
<212> TYPE: DNA
<213> ORGANISM: Artificial sequence
<220> FEATURE:
<223> OTHER INFORMATION: modified GFAT1Alt by an internal purification tag
<220> FEATURE:
<221> NAME/KEY: CDS
<222> LOCATION: (1)..(2118)
<223> OTHER INFORMATION:
<220> FEATURE:
<221> NAME/KEY: misc_feature
<222> LOCATION: (170)..(170)
<223> OTHER INFORMATION: t or c

<400> SEQUENCE: 11

```
atg tgt ggt ata ttt gct tac tta aac tac cat gtt cct cga acg aga      48
Met Cys Gly Ile Phe Ala Tyr Leu Asn Tyr His Val Pro Arg Thr Arg
1               5                  10                  15 cga gaa atc ctg gag acc cta atc aaa ggc ctt cag aga ctg gag tac      96
Arg Glu Ile Leu Glu Thr Leu Ile Lys Gly Leu Gln Arg Leu Glu Tyr
            20                  25                  30 aga gga tat gat tct gct ggt gtg gga ttt gat gga ggc aat gat aaa     144
Arg Gly Tyr Asp Ser Ala Gly Val Gly Phe Asp Gly Gly Asn Asp Lys
        35                  40                  45 gat tgg gaa gcc aat gcc tgc aaa anc cag ctt att aag aag aaa gga     192
Asp Trp Glu Ala Asn Ala Cys Lys Xaa Gln Leu Ile Lys Lys Lys Gly
    50                  55                  60 aaa gtt aag gca ctg gat gaa gaa gtt cac aag caa caa gat atg gat     240
Lys Val Lys Ala Leu Asp Glu Glu Val His Lys Gln Gln Asp Met Asp
65                  70                  75                  80 ttg gat ata gaa ttt gat gta cac ctt gga ata gct cat acc cgt tgg     288
Leu Asp Ile Glu Phe Asp Val His Leu Gly Ile Ala His Thr Arg Trp
                85                  90                  95 gca aca cat gga gaa ccc agt cct gtc aat agc cac ccc cag cgc tct     336
Ala Thr His Gly Glu Pro Ser Pro Val Asn Ser His Pro Gln Arg Ser
            100                 105                 110 gat aaa aat aat gaa ttt atc gtt att cac aat gga atc atc acc aac     384
Asp Lys Asn Asn Glu Phe Ile Val Ile His Asn Gly Ile Ile Thr Asn
        115                 120                 125 tac aaa gac ttg aaa aag ttt ttg gaa agc aaa ggc tat gac ttc gaa     432
Tyr Lys Asp Leu Lys Lys Phe Leu Glu Ser Lys Gly Tyr Asp Phe Glu
    130                 135                 140 tct gaa aca gac aca gag aca att gcc aag ctc gtt aag tat atg tat     480
Ser Glu Thr Asp Thr Glu Thr Ile Ala Lys Leu Val Lys Tyr Met Tyr
145                 150                 155                 160 gac aat cgg gaa agt caa gat acc agc ttt act acc ttg gtg gag aga     528
Asp Asn Arg Glu Ser Gln Asp Thr Ser Phe Thr Thr Leu Val Glu Arg
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 165 |     |     |     |     | 170 |     |     |     |     | 175 |     |     |     |      |
| gtt | atc | caa | caa | ttg | gaa | ggt | gct | ttt | gca | ctt | gtg | ttt | aaa | agt | gtt | 576  |
| Val | Ile | Gln | Gln | Leu | Glu | Gly | Ala | Phe | Ala | Leu | Val | Phe | Lys | Ser | Val |      |
|     |     |     | 180 |     |     |     |     | 185 |     |     |     |     | 190 |     |     |      |
| cat | ttt | ccc | ggg | caa | gca | gtt | ggc | aca | agg | cga | ggt | agc | cct | ctg | ttg | 624  |
| His | Phe | Pro | Gly | Gln | Ala | Val | Gly | Thr | Arg | Arg | Gly | Ser | Pro | Leu | Leu |      |
|     |     | 195 |     |     |     |     | 200 |     |     |     |     | 205 |     |     |     |      |
| att | ggt | gta | cgg | agt | gaa | cat | aaa | ctt | tct | act | gat | cac | att | cct | ata | 672  |
| Ile | Gly | Val | Arg | Ser | Glu | His | Lys | Leu | Ser | Thr | Asp | His | Ile | Pro | Ile |      |
|     | 210 |     |     |     |     | 215 |     |     |     |     | 220 |     |     |     |     |      |
| ctc | tac | aga | aca | gct | agg | act | cag | att | gga | tca | aaa | ttc | aca | cgg | tgg | 720  |
| Leu | Tyr | Arg | Thr | Ala | Arg | Thr | Gln | Ile | Gly | Ser | Lys | Phe | Thr | Arg | Trp |      |
| 225 |     |     |     |     | 230 |     |     |     |     | 235 |     |     |     |     | 240 |      |
| gga | tca | cag | gga | gaa | aga | ggc | aaa | gac | aag | aaa | gga | agc | tgc | aat | ctc | 768  |
| Gly | Ser | Gln | Gly | Glu | Arg | Gly | Lys | Asp | Lys | Lys | Gly | Ser | Cys | Asn | Leu |      |
|     |     |     |     | 245 |     |     |     |     | 250 |     |     |     |     | 255 |     |      |
| tct | cgt | gtg | gac | agc | aca | acc | tgc | ctt | ttc | ccg | gtg | gaa | gaa | aaa | gca | 816  |
| Ser | Arg | Val | Asp | Ser | Thr | Thr | Cys | Leu | Phe | Pro | Val | Glu | Glu | Lys | Ala |      |
|     |     |     | 260 |     |     |     |     | 265 |     |     |     |     | 270 |     |     |      |
| gtg | gag | tat | tac | ttt | gct | tct | gat | gca | agt | gct | gtc | ata | gaa | cac | acc | 864  |
| Val | Glu | Tyr | Tyr | Phe | Ala | Ser | Asp | Ala | Ser | Ala | Val | Ile | Glu | His | Thr |      |
|     |     | 275 |     |     |     |     | 280 |     |     |     |     | 285 |     |     |     |      |
| aat | cgc | gtc | atc | ttt | ctg | gaa | gat | gat | gat | gtt | gca | gca | gta | gtg | gat | 912  |
| Asn | Arg | Val | Ile | Phe | Leu | Glu | Asp | Asp | Asp | Val | Ala | Ala | Val | Val | Asp |      |
|     | 290 |     |     |     |     | 295 |     |     |     |     | 300 |     |     |     |     |      |
| gga | cgt | ctt | tct | atc | cat | cga | att | aaa | cga | act | gca | gga | cat | cac | cat | 960  |
| Gly | Arg | Leu | Ser | Ile | His | Arg | Ile | Lys | Arg | Thr | Ala | Gly | His | His | His |      |
| 305 |     |     |     |     | 310 |     |     |     |     | 315 |     |     |     |     | 320 |      |
| cac | cat | cac | gat | cac | ccc | gga | cga | gct | gtg | caa | aca | ctc | cag | atg | gaa | 1008 |
| His | His | His | Asp | His | Pro | Gly | Arg | Ala | Val | Gln | Thr | Leu | Gln | Met | Glu |      |
|     |     |     |     | 325 |     |     |     |     | 330 |     |     |     |     | 335 |     |      |
| ctc | cag | cag | atc | atg | aag | ggc | aac | ttc | agt | tca | ttt | atg | cag | aag | gaa | 1056 |
| Leu | Gln | Gln | Ile | Met | Lys | Gly | Asn | Phe | Ser | Ser | Phe | Met | Gln | Lys | Glu |      |
|     |     |     | 340 |     |     |     |     | 345 |     |     |     |     | 350 |     |     |      |
| ata | ttt | gag | cag | cca | gag | tct | gtc | gtg | aac | aca | atg | aga | gga | aga | gtc | 1104 |
| Ile | Phe | Glu | Gln | Pro | Glu | Ser | Val | Val | Asn | Thr | Met | Arg | Gly | Arg | Val |      |
|     |     | 355 |     |     |     |     | 360 |     |     |     |     | 365 |     |     |     |      |
| aac | ttt | gat | gac | tat | act | gtg | aat | ttg | ggt | ggt | ttg | aag | gat | cac | ata | 1152 |
| Asn | Phe | Asp | Asp | Tyr | Thr | Val | Asn | Leu | Gly | Gly | Leu | Lys | Asp | His | Ile |      |
|     | 370 |     |     |     |     | 375 |     |     |     |     | 380 |     |     |     |     |      |
| aag | gag | atc | cag | aga | tgc | cgg | cgt | ttg | att | ctt | att | gct | tgt | gga | aca | 1200 |
| Lys | Glu | Ile | Gln | Arg | Cys | Arg | Arg | Leu | Ile | Leu | Ile | Ala | Cys | Gly | Thr |      |
| 385 |     |     |     |     | 390 |     |     |     |     | 395 |     |     |     |     | 400 |      |
| agt | tac | cat | gct | ggt | gta | gca | aca | cgt | caa | gtt | ctt | gag | gag | ctg | act | 1248 |
| Ser | Tyr | His | Ala | Gly | Val | Ala | Thr | Arg | Gln | Val | Leu | Glu | Glu | Leu | Thr |      |
|     |     |     |     | 405 |     |     |     |     | 410 |     |     |     |     | 415 |     |      |
| gag | ttg | cct | gtg | atg | gtg | gaa | cta | gca | agt | gac | ttc | ctg | gac | aga | aac | 1296 |
| Glu | Leu | Pro | Val | Met | Val | Glu | Leu | Ala | Ser | Asp | Phe | Leu | Asp | Arg | Asn |      |
|     |     |     | 420 |     |     |     |     | 425 |     |     |     |     | 430 |     |     |      |
| aca | cca | gtc | ttt | cga | gat | gat | gtt | tgc | ttt | ttc | ctt | agt | caa | tca | ggt | 1344 |
| Thr | Pro | Val | Phe | Arg | Asp | Asp | Val | Cys | Phe | Phe | Leu | Ser | Gln | Ser | Gly |      |
|     |     | 435 |     |     |     |     | 440 |     |     |     |     | 445 |     |     |     |      |
| gag | aca | gca | gat | act | ttg | atg | ggt | ctt | cgt | tac | tgt | aag | gag | aga | gga | 1392 |
| Glu | Thr | Ala | Asp | Thr | Leu | Met | Gly | Leu | Arg | Tyr | Cys | Lys | Glu | Arg | Gly |      |
|     | 450 |     |     |     |     | 455 |     |     |     |     | 460 |     |     |     |     |      |
| gct | tta | act | gtg | ggg | atc | aca | aac | aca | gtt | ggc | agt | tcc | ata | tca | cgg | 1440 |
| Ala | Leu | Thr | Val | Gly | Ile | Thr | Asn | Thr | Val | Gly | Ser | Ser | Ile | Ser | Arg |      |
| 465 |     |     |     |     | 470 |     |     |     |     | 475 |     |     |     |     | 480 |      |
| gag | aca | gat | tgt | gga | gtt | cat | att | aat | gct | ggt | cct | gag | att | ggt | gtg | 1488 |

```
                                                                                  -continued
Glu Thr Asp Cys Gly Val His Ile Asn Ala Gly Pro Glu Ile Gly Val
                485                 490                 495 gcc agt aca aag gct tat acc agc cag ttt gta tcc ctt gtg atg ttt       1536
Ala Ser Thr Lys Ala Tyr Thr Ser Gln Phe Val Ser Leu Val Met Phe
            500                 505                 510 gcc ctt atg atg tgt gat gat cgg atc tcc atg caa gaa aga cgc aaa       1584
Ala Leu Met Met Cys Asp Asp Arg Ile Ser Met Gln Glu Arg Arg Lys
        515                 520                 525 gag atc atg ctt gga ttg aaa cgg ctg cct gat ttg att aag gaa gta       1632
Glu Ile Met Leu Gly Leu Lys Arg Leu Pro Asp Leu Ile Lys Glu Val
    530                 535                 540 ctg agc atg gat gac gaa att cag aaa cta gca aca gaa ctt tat cat       1680
Leu Ser Met Asp Asp Glu Ile Gln Lys Leu Ala Thr Glu Leu Tyr His
545                 550                 555                 560 cag aag tca gtt ctg ata atg gga cga ggc tat cat tat gct act tgt       1728
Gln Lys Ser Val Leu Ile Met Gly Arg Gly Tyr His Tyr Ala Thr Cys
                565                 570                 575 ctt gaa ggg gca ctg aaa atc aaa gaa att act tat atg cac tct gaa       1776
Leu Glu Gly Ala Leu Lys Ile Lys Glu Ile Thr Tyr Met His Ser Glu
            580                 585                 590 ggc atc ctt gct ggt gaa ttg aaa cat ggc cct ctg gct ttg gtg gat       1824
Gly Ile Leu Ala Gly Glu Leu Lys His Gly Pro Leu Ala Leu Val Asp
        595                 600                 605 aaa ttg atg cct gtg atc atg atc atc atg aga gat cac act tat gcc       1872
Lys Leu Met Pro Val Ile Met Ile Ile Met Arg Asp His Thr Tyr Ala
    610                 615                 620 aag tgt cag aat gct ctt cag caa gtg gtt gct cgg cag ggg cgg cct       1920
Lys Cys Gln Asn Ala Leu Gln Gln Val Val Ala Arg Gln Gly Arg Pro
625                 630                 635                 640 gtg gta att tgt gat aag gag gat act gag acc att aag aac aca aaa       1968
Val Val Ile Cys Asp Lys Glu Asp Thr Glu Thr Ile Lys Asn Thr Lys
                645                 650                 655 aga acg atc aag gtg ccc cac tca gtg gac tgc ttg cag ggc att ctc       2016
Arg Thr Ile Lys Val Pro His Ser Val Asp Cys Leu Gln Gly Ile Leu
            660                 665                 670 agc gtg atc cct tta cag ttg ctg gct ttc cac ctt gct gtg ctg aga       2064
Ser Val Ile Pro Leu Gln Leu Leu Ala Phe His Leu Ala Val Leu Arg
        675                 680                 685 ggc tat gat gtt gat ttc cca cgg aat ctt gcc aaa tct gtg act gta       2112
Gly Tyr Asp Val Asp Phe Pro Arg Asn Leu Ala Lys Ser Val Thr Val
    690                 695                 700 gag tga                                                               2118
Glu
705

<210> SEQ ID NO 12
<211> LENGTH: 705
<212> TYPE: PRT
<213> ORGANISM: Artificial sequence
<220> FEATURE:
<221> NAME/KEY: misc_feature
<222> LOCATION: (57)..(57)
<223> OTHER INFORMATION: 'Xaa' in position 57 represents Thr or Ile
<220> FEATURE:
<223> OTHER INFORMATION: modified GFAT1Alt by an internal purification
      tag

<400> SEQUENCE: 12

Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30
```

```
Arg Gly Tyr Asp Ser Ala Gly Val Gly Phe Asp Gly Gly Asn Asp Lys
            35                  40                  45

Asp Trp Glu Ala Asn Ala Cys Lys Xaa Gln Leu Ile Lys Lys Lys Gly
 50                  55                  60

Lys Val Lys Ala Leu Asp Glu Glu Val His Lys Gln Gln Asp Met Asp
 65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser
                100                 105                 110

Asp Lys Asn Asn Glu Phe Ile Val Ile His Asn Gly Ile Ile Thr Asn
            115                 120                 125

Tyr Lys Asp Leu Lys Lys Phe Leu Glu Ser Lys Gly Tyr Asp Phe Glu
130                 135                 140

Ser Glu Thr Asp Thr Glu Thr Ile Ala Lys Leu Val Lys Tyr Met Tyr
145                 150                 155                 160

Asp Asn Arg Glu Ser Gln Asp Thr Ser Phe Thr Thr Leu Val Glu Arg
                165                 170                 175

Val Ile Gln Gln Leu Glu Gly Ala Phe Ala Leu Val Phe Lys Ser Val
            180                 185                 190

His Phe Pro Gly Gln Ala Val Gly Thr Arg Arg Gly Ser Pro Leu Leu
            195                 200                 205

Ile Gly Val Arg Ser Glu His Lys Leu Ser Thr Asp His Ile Pro Ile
            210                 215                 220

Leu Tyr Arg Thr Ala Arg Thr Gln Ile Gly Ser Lys Phe Thr Arg Trp
225                 230                 235                 240

Gly Ser Gln Gly Glu Arg Gly Lys Asp Lys Lys Gly Ser Cys Asn Leu
                245                 250                 255

Ser Arg Val Asp Ser Thr Thr Cys Leu Phe Pro Val Glu Glu Lys Ala
                260                 265                 270

Val Glu Tyr Tyr Phe Ala Ser Asp Ala Ser Ala Val Ile Glu His Thr
            275                 280                 285

Asn Arg Val Ile Phe Leu Glu Asp Asp Val Ala Ala Val Val Asp
            290                 295                 300

Gly Arg Leu Ser Ile His Arg Ile Lys Arg Thr Ala Gly His His His
305                 310                 315                 320

His His His Asp His Pro Gly Arg Ala Val Gln Thr Leu Gln Met Glu
                325                 330                 335

Leu Gln Gln Ile Met Lys Gly Asn Phe Ser Ser Phe Met Gln Lys Glu
            340                 345                 350

Ile Phe Glu Gln Pro Glu Ser Val Val Asn Thr Met Arg Gly Arg Val
            355                 360                 365

Asn Phe Asp Asp Tyr Thr Val Asn Leu Gly Gly Leu Lys Asp His Ile
            370                 375                 380

Lys Glu Ile Gln Arg Cys Arg Arg Leu Ile Leu Ile Ala Cys Gly Thr
385                 390                 395                 400

Ser Tyr His Ala Gly Val Ala Thr Arg Gln Val Leu Glu Glu Leu Thr
                405                 410                 415

Glu Leu Pro Val Met Val Glu Leu Ala Ser Asp Phe Leu Asp Arg Asn
            420                 425                 430

Thr Pro Val Phe Arg Asp Asp Val Cys Phe Phe Leu Ser Gln Ser Gly
            435                 440                 445
```

```
Glu Thr Ala Asp Thr Leu Met Gly Leu Arg Tyr Cys Lys Glu Arg Gly
    450                 455                 460

Ala Leu Thr Val Gly Ile Thr Asn Thr Val Gly Ser Ser Ile Ser Arg
465                 470                 475                 480

Glu Thr Asp Cys Gly Val His Ile Asn Ala Gly Pro Glu Ile Gly Val
                485                 490                 495

Ala Ser Thr Lys Ala Tyr Thr Ser Gln Phe Val Ser Leu Val Met Phe
            500                 505                 510

Ala Leu Met Met Cys Asp Asp Arg Ile Ser Met Gln Glu Arg Arg Lys
        515                 520                 525

Glu Ile Met Leu Gly Leu Lys Arg Leu Pro Asp Leu Ile Lys Glu Val
    530                 535                 540

Leu Ser Met Asp Asp Glu Ile Gln Lys Leu Ala Thr Glu Leu Tyr His
545                 550                 555                 560

Gln Lys Ser Val Leu Ile Met Gly Arg Gly Tyr His Tyr Ala Thr Cys
                565                 570                 575

Leu Glu Gly Ala Leu Lys Ile Lys Glu Ile Thr Tyr Met His Ser Glu
            580                 585                 590

Gly Ile Leu Ala Gly Glu Leu Lys His Gly Pro Leu Ala Leu Val Asp
        595                 600                 605

Lys Leu Met Pro Val Ile Met Ile Met Arg Asp His Thr Tyr Ala
    610                 615                 620

Lys Cys Gln Asn Ala Leu Gln Gln Val Val Ala Arg Gln Gly Arg Pro
625                 630                 635                 640

Val Val Ile Cys Asp Lys Glu Asp Thr Glu Thr Ile Lys Asn Thr Lys
                645                 650                 655

Arg Thr Ile Lys Val Pro His Ser Val Asp Cys Leu Gln Gly Ile Leu
            660                 665                 670

Ser Val Ile Pro Leu Gln Leu Leu Ala Phe His Leu Ala Val Leu Arg
        675                 680                 685

Gly Tyr Asp Val Asp Phe Pro Arg Asn Leu Ala Lys Ser Val Thr Val
    690                 695                 700

Glu
705

<210> SEQ ID NO 13
<211> LENGTH: 608
<212> TYPE: PRT
<213> ORGANISM: Escherichia coli

<400> SEQUENCE: 13

Cys Gly Ile Val Gly Ala Ile Ala Gln Arg Asp Val Ala Glu Ile Leu
1               5                   10                  15

Leu Glu Gly Leu Arg Arg Leu Glu Tyr Arg Gly Tyr Asp Ser Ala Gly
            20                  25                  30

Leu Ala Val Val Asp Ala Glu Gly His Met Thr Arg Leu Arg Arg Leu
        35                  40                  45

Gly Lys Val Gln Met Leu Ala Gln Ala Ala Glu Glu His Pro Leu His
    50                  55                  60

Gly Gly Thr Gly Ile Ala His Thr Arg Trp Ala Thr His Gly Glu Pro
65                  70                  75                  80

Ser Glu Val Asn Ala His Pro His Val Ser Glu His Ile Val Val Val
                85                  90                  95

His Asn Gly Ile Ile Glu Asn His Glu Pro Leu Arg Glu Glu Leu Lys
            100                 105                 110
```

```
Ala Arg Gly Tyr Thr Phe Val Ser Glu Thr Asp Thr Glu Val Ile Ala
            115                 120                 125

His Leu Val Asn Trp Glu Leu Lys Gln Gly Gly Thr Leu Arg Glu Ala
130                 135                 140

Val Leu Arg Ala Ile Pro Gln Leu Arg Gly Ala Tyr Gly Thr Val Ile
145                 150                 155                 160

Met Asp Ser Arg His Pro Asp Thr Leu Leu Ala Arg Ser Gly Ser
                165                 170                 175

Pro Leu Val Ile Gly Leu Gly Met Gly Glu Asn Phe Ile Ala Ser Asp
                180                 185                 190

Gln Leu Ala Leu Leu Pro Val Thr Arg Arg Phe Ile Phe Leu Glu Glu
            195                 200                 205

Gly Asp Ile Ala Glu Ile Thr Arg Arg Ser Val Asn Ile Phe Asp Lys
        210                 215                 220

Thr Gly Ala Glu Val Lys Arg Gln Asp Ile Glu Ser Asn Leu Gln Tyr
225                 230                 235                 240

Asp Ala Gly Asp Lys Gly Ile Tyr Arg His Tyr Met Gln Lys Glu Ile
                245                 250                 255

Tyr Glu Gln Pro Asn Ala Ile Lys Asn Thr Leu Thr Gly Arg Ile Ser
                260                 265                 270

His Gly Gln Val Asp Leu Ser Glu Leu Gly Pro Asn Ala Asp Glu Leu
            275                 280                 285

Leu Ser Lys Val Glu His Ile Gln Ile Leu Ala Cys Gly Thr Ser Tyr
        290                 295                 300

Asn Ser Gly Met Val Ser Arg Tyr Trp Phe Glu Ser Leu Ala Gly Ile
305                 310                 315                 320

Pro Cys Asp Val Glu Ile Ala Ser Glu Phe Arg Tyr Arg Lys Ser Ala
                325                 330                 335

Val Arg Arg Asn Ser Leu Met Ile Thr Leu Ser Gln Ser Gly Glu Thr
            340                 345                 350

Ala Asp Thr Leu Ala Gly Leu Arg Leu Ser Lys Glu Leu Gly Tyr Leu
        355                 360                 365

Gly Ser Leu Ala Ile Cys Asn Val Pro Gly Ser Ser Leu Val Arg Glu
370                 375                 380

Ser Asp Leu Ala Leu Met Thr Asn Ala Gly Thr Glu Ile Gly Val Ala
385                 390                 395                 400

Ser Thr Lys Ala Phe Thr Thr Gln Leu Thr Val Leu Leu Met Leu Val
                405                 410                 415

Ala Lys Leu Ser Arg Leu Lys Gly Leu Asp Ala Ser Ile Glu His Asp
            420                 425                 430

Ile Val His Gly Leu Gln Ala Leu Pro Ser Arg Ile Glu Gln Met Leu
        435                 440                 445

Ser Gln Asp Lys Arg Ile Glu Ala Leu Ala Glu Asp Phe Ser Asp Lys
            450                 455                 460

His His Ala Leu Phe Leu Gly Arg Gly Asp Gln Tyr Pro Ile Ala Leu
465                 470                 475                 480

Glu Gly Ala Leu Lys Leu Lys Glu Ile Ser Tyr Ile His Ala Glu Ala
                485                 490                 495

Tyr Ala Ala Gly Glu Leu Lys His Gly Pro Leu Ala Leu Ile Asp Ala
                500                 505                 510

Asp Met Pro Val Ile Val Val Ala Pro Asn Asn Glu Leu Leu Glu Lys
            515                 520                 525
```

```
Leu Lys Ser Asn Ile Glu Glu Val Arg Ala Arg Gly Gly Gln Leu Tyr
        530                 535                 540

Val Phe Ala Asp Gln Asp Ala Gly Phe Val Ser Ser Asp Asn Met His
545                 550                 555                 560

Ile Ile Glu Met Pro His Val Glu Glu Val Ile Ala Pro Ile Phe Tyr
                565                 570                 575

Thr Val Pro Leu Gln Leu Leu Ala Tyr His Val Ala Leu Ile Lys Gly
            580                 585                 590

Thr Asp Val Asp Gln Pro Arg Asn Leu Ala Lys Ser Val Thr Val Glu
        595                 600                 605

<210> SEQ ID NO 14
<211> LENGTH: 72
<212> TYPE: DNA
<213> ORGANISM: Artificial sequence
<220> FEATURE:
<223> OTHER INFORMATION: Primer

<400> SEQUENCE: 14
tggacgtctt tctatccatc gaattaaacg aactgcagga catcaccatc accatcacga      60
tcaccccgga cg                                                         72

<210> SEQ ID NO 15
<211> LENGTH: 44
<212> TYPE: DNA
<213> ORGANISM: Artificial sequence
<220> FEATURE:
<223> OTHER INFORMATION: Primer

<400> SEQUENCE: 15
caaagttgac tcttcctctc attgtgttca cgacagactc tggc                      44

<210> SEQ ID NO 16
<211> LENGTH: 43
<212> TYPE: DNA
<213> ORGANISM: Artificial sequence
<220> FEATURE:
<223> OTHER INFORMATION: Primer

<400> SEQUENCE: 16
aatctagatt catgctcgag cggccgccag tgtgattgat atc                       43

<210> SEQ ID NO 17
<211> LENGTH: 36
<212> TYPE: DNA
<213> ORGANISM: Artificial sequence
<220> FEATURE:
<223> OTHER INFORMATION: Primer

<400> SEQUENCE: 17
atttttatca gagcgctggg ggtggctatt gacagg                               36

<210> SEQ ID NO 18
<211> LENGTH: 8
<212> TYPE: PRT
<213> ORGANISM: Artificial sequence
<220> FEATURE:
<223> OTHER INFORMATION: FLAG tag

<400> SEQUENCE: 18

Asp Thr Lys Asp Asp Asp Asp Lys
1               5
```

```
<210> SEQ ID NO 19
<211> LENGTH: 6
<212> TYPE: PRT
<213> ORGANISM: Artificial sequence
<220> FEATURE:
<223> OTHER INFORMATION: hexa-histidine tag

<400> SEQUENCE: 19

His His His His His His
1               5
```

GLUTAMINE:FRUCTOSE-6-PHOSPHATE AMIDOTRANSFERASE (GFAT) COMPRISING AN INTERNAL PURIFICATION MARKER AND USE THEREOF FOR THE SCREENING OF COMPOUNDS

BACKGROUND OF THE INVENTION

1. Field of the Invention

The present invention relates to a modified glutamine:fructose-6-phosphate amidotransferase, which can be rapidly purified in quantities sufficient for the screening of compounds modifying its activity.

2. Description of the Related Art

Glutamine:fructose-6-phosphate amidotransferases (GFAT), EC 2.6.1.16, also called glucosamine-6-phosphate synthases or 2-deoxy-glucose-6-phosphate ketol isomerases, are involved in the biosynthesis route of hexosamines. GFAT catalyzes the first, limiting, stage of this biosynthesis route according to the reaction:

L-Glutamine+fructose-6-phosphate→L-Glutamate+ glucosamine-6-phosphate by transfer of the amidic nitrogen from the L-Glutamine to the ketone function of the fructose-6-phosphate. The GFATs therefore control the flow of glucose in the route of the hexosamines, via the fructose-6-phosphate, and consequently the formation of the hexosamines produced.

A recombinant bacterial form of GFAT, the glucosamine-6-phosphate synthase of *Escherichia coli*, has been purified to homogeneity and studied exhaustively. The properties and the enzymatic mechanism of the amide transfer have in particular been widely described (article by Teplyakov et al., *Nat. Prod. Rep.* (2002) 19:60). In particular, this enzyme, the crystalline structure of which has been resolved (Teplyakov et al., *J. Mol. Biol.* (2001) 313:1093), is formed by two domains, one having a hydrolase activity (glutaminase) and the other an isomerase activity.

Moreover, eukaryotic GFATs have been characterized, including in particular that of rat liver (Huynh et al., *Arch. Biochem. Biophys.* (2000) 379:307) and that of the yeast *Candida albicans* (Milewsky et al., *J. Biol. Chem.* (1999) 274:4000).

In humans, preliminary studies have shown the presence of GFAT activity in the liver (Ghosh et al., *J. Biol. Chem.* (1960) 235:1265). Several GFATs are now known. GFAT1, the principal form, GFAT2, which is preferentially expressed in the central nervous system, and GFAT1Alt, an isoform of GFAT1, essentially expressed in the striated muscles. The peptide sequences of GFAT1 and GFAT2 possess 75% sequence identity with each other, and those of GFAT1 and GFAT1Alt are identical except for an insertion of 18 amino acids into the GFAT1Alt sequence. The sequences of GFAT are therefore very preserved in humans, but also between species, since the peptide sequences of human GFAT1 and *E. coli* GFAT or mouse GFAT1 have 35% and 99% identity respectively.

The human GFAT1 gene was cloned in 1992 (McKnight et al., *J. Biol. Chem.* (1992) 267:25208). It codes a protein of 77 kDa formed by two distinct domains (Teplyakov et al., *Nat. Prod. Rep.* (2002) 19:60).

The increase in the production of UDP-NAc-GlcNH$_2$, the final product of the biosynthesis route of the hexosamines, and its accumulation in the tissues have recently been involved in the development of insulin-resistance (Marshall et al., *FASEB J.* (1991) 5:3031, Yki-Jarvinen et al., *Diabetes* (1996) 45:302, Thompson et al., *J. Biol. Chem.* (1997) 272:7759, Hawkins et al., *J. Clin. Invest.* (1997) 99:2173, Robinson et al., *Diabetes* (1993) 42:1333, Daniels et al., *J. Clin. Invest.* (1995) 96:1235, Baron et al., *J. Clin. Invest.* (1995) 96:2792).

Thus, it has been shown that an increase in the cell level of UDP-NAc-GlcNH$_2$ by a slight overexpression of GFAT1, or a supply of exogenic glucosamine, can induce insulin-resistance both in vivo and in adipocytes in culture (Robinson et al., *Diabetes* (1993) 42:1333, Daniels et al., *J. Clin. Invest.* (1995) 96:1235, Baron et al., *J. Clin. Invest.* (1995) 96:2792, Hebert et al., *J. Clin. Invest.* (1996) 98:930).

In fact, insulin activates its transduction route by binding to its receptor, which induces the translocation of the glucose transporters, such as the GLUT4 receptor, stored in the cell, towards the membrane, and increases the inflow of glucose. The glucose thus enters the glycolysis route and is converted to glucose-6-phosphate then to fructose-6-phosphate. When the inflow of glucose is excessive, the fructose-6-phosphate enters the biosynthesis route of the hexosamines and is converted to glucosamine-6-phosphate by the GFAT. Several observations indicate that the metabolites of the glucosamine-6-phosphate prevent the translocation of the glucose receptors towards the cell membrane, thus reducing the inflow of the cell glucose (Marshall et al., *FASEB J.* (1991) 5:3031, Giacarri et al., *Diabetologia* (1995) 38:518, Marshall et al., *J. Biol. Chem.* (1991) 266:4706, Paterson et al., *Endocrinology* (1995) 136:2809).

The mechanism by which the metabolites of the glucosamine-6-phosphate exercise their physiological effects is not clear. One hypothesis has however been proposed: a high cytosolic concentration of UDP-NAc-GlcNH$_2$ would lead to the hyperglycosylation of the Ser or Thr phosphorylation sites, thus leading to the stopping of the insulin-signalling route (Comer et al., *J. Biol. Chem.* (2000) 275:29179).

The GFAT activity is therefore considered as being one of the causes of high levels of blood glucose; moreover it is known to be high in patients suffering from non-insulin-dependant sugar diabetes or type II diabetes (Yki-Jarvinen et al., *Diabetes* (1996) 45:302).

Obtaining GFAT inhibitors would make it possible to reduce glycaemia in particular in individuals suffering from pathologies linked to hyperglycaemia, such as type II diabetes, acidosis and/or diabetic ketosis, for example.

Fungal or plant GFAT inhibitors could also make it possible to obtain fungicides and herbicides respectively.

However, in spite of the obtaining of recombinant forms of GFAT, the instability of the enzymatic preparations obtained, their small quantity, and their insufficient purification level, have not made it possible to obtain effective GFAT inhibitors.

SUMMARY OF THE INVENTION

A subject of the invention is therefore to provide a modified GFAT the activity of which is stable and which can be obtained in a large quantity, with a high level of purity and of activity.

The present invention relates to an enzymatically-active protein comprising:
- a GFAT sequence and at least one purification tag sequence, the purification tag sequence being inserted between two consecutive amino acids of the GFAT sequence, or
- a sequence deriving from the preceding sequence by suppression, insertion or mutation of at least one amino acid, provided that said protein has an enzyme activity, or a sequence having at least 35%, in particular at least 90%, of sequence identity and/or at least 44%, in particular at least 95%, of sequence similarity with one of the preceding sequences, provided that said protein has an enzyme activity.

The term GFAT designates a class E.C. 2.6.1.16 enzyme catalyzing the following reaction:

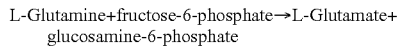
L-Glutamine+fructose-6-phosphate→L-Glutamate+ glucosamine-6-phosphate in particular under the experimental conditions as described in the example which follows or in Broschat et al., *J. Biol. Chem.* (2002) 277:14764.

GFAT is designated by the name of glutamine:fructose-6-phosphate amidotransferase, or also glucosamine-6-phosphate synthase or 2-deoxy-glucose-6-phosphate ketol isomerase.

The term "enzymatically-active protein" designates a protein having a catalytic action.

Advantageously, the enzymatically-active protein possesses a GFAT activity.

The term "purification tag" designates a peptide sequence capable of binding specifically to a given ligand. Advantageously, the binding of said ligand to the purification tag makes it possible to form a complex between the protein carrying the purification tag and said ligand, said complex being able to be specifically isolated.

Advantageously, the purification tags according to the invention are not placed at the end of the peptide chain, at the N-terminal or C-terminal end, but inside the peptide chain.

The term "sequence identity" designates the percentage of identical amino acids between two aligned sequences, in particular using algorithms such as that defined by Altschul et al., *Nucleic Acids Res.* (1997) 25:3389, for example.

The term "sequence similarity" designates the percentage of similar amino acids, i.e. amino acids the side chains of which possess similar physico-chemical properties, between two aligned sequences, in particular using algorithms as defined by Altschul et al., *Nucleic Acids Res.* (1997) 25:3389, for example.

The present invention relates in particular to a protein as defined above, in which the GFAT sequence corresponds to a bacterial or eukaryotic, in particular plant, fungal or animal, in particular insect or mammal, more particularly human GFAT sequence.

The invention relates more particularly to a protein as defined above, in which the purification tag sequence is inserted between two consecutive amino acids of the GFAT sequence, said amino acids being included in:
 a part of the GFAT sequence corresponding and/or being homologous to the sequence extending between the β2 sheet and the β3 sheet of the *Escherichia coli* GFAT, or
 a part of the GFAT sequence corresponding and/or being homologous to the sequence extending between the β13 sheet and the β14 sheet of the *Escherichia coli* GFAT, or
 a part of the GFAT sequence corresponding and/or being homologous to the sequence extending between the β15 sheet and the α6 helix of the *Escherichia coli* GFAT.

The structure of the *Escherichia coli* GFAT is described in particular by Teplyakov et al., *J. Mol. Biol.* (2001) 313:1093 (whole protein), by Isupov et al., *Structure* (1996) 4:801 (glutaminase domain) and by Teplyakov et al., *Structure* (1998) 6:1047 (isomerase domain). The structure of the complete protein can in particular be consulted using the 1JXA atomic coordinates file filed with the *Protein Data Bank* (http://www.pdb.org).

The *E. coli* GFAT peptide sequence is defined by SEQ ID NO: 13.

The sequence extending between the β2 sheet and the β3 sheet corresponds to the sequence extending approximately between amino acids 30 to 80 of *E. coli* GFAT, situated in the glutaminase domain.

The sequence extending between the β13 sheet and the β14 sheet corresponds to the sequence extending approximately between amino acids 220 to 230 of *E. coli* GFAT, situated in the glutaminase domain.

The sequence extending between the β15 sheet and the α6 helix corresponds to the sequence extending approximately between amino acids 235 to 250 of *E. coli* GFAT, situated in the isomerase domain.

According to a particular embodiment, the invention therefore relates to a protein as defined above, in which the purification tag sequence is inserted between two consecutive amino acids of the GFAT sequence, said amino acids being included in:
 a part of the GFAT sequence corresponding and/or being homologous to the sequence extending approximately between amino acids 30 to 80 of *Escherichia coli* GFAT, or
 a part of the GFAT sequence corresponding and/or being homologous to the sequence extending approximately between amino acids 220 to 230 of *Escherichia coli* GFAT, or
 a part of the GFAT sequence corresponding and/or being homologous to the sequence extending approximately between amino acids 235 to 250 of *Escherichia coli* GFAT.

Identification of the parts of GFAT sequences corresponding and/or being homologous to secondary structures of *E. coli* GFAT can be obtained by aligning the sequence of said GFAT with that of *E. coli* GFAT, in particular using an algorithm such as that defined by Altschul et al., *Nucleic Acids Res.* (1997) 25:3389 or using the Clustal W software, well known to a person skilled in the art and described by Thompson et al., *Nucleic Acids Res.* (1994) 22: 4673-4680, for example.

In particular, two sequences or parts of sequences are referred to as homologous if the percentage of identity between these two sequences or parts of sequences is greater than approximately 35% and/or if the percentage of similarity between these two sequences or parts of sequences is greater than approximately 44%.

More particularly, two sequences or parts of sequences are referred to as homologous if they are capable of hybridizing under stringent conditions, such as the following conditions: formamide 50%, NaCl 0.75 mol/l, sodium citrate 0.75 mmol/l, sodium dodecyl sulphate 1%, pH 7, 42° C.

According to another preferred embodiment, the invention relates to a protein as defined above, in which the purification tag sequence is inserted between two consecutive amino acids of a human GFAT sequence, said amino acids being included between amino acids 40 to 50, 290 to 330, and/or 340 to 370 of said human GFAT sequence.

Amino acids 40 to 50 of said human GFAT sequence correspond and/or are homologous to the part of the *E. coli* GFAT sequence extending between the β2 sheet and the β3 sheet, i.e. to the sequence extending approximately between amino acids 30 to 80 of *E. coli* GFAT.

Amino acids 290 to 330 of said human GFAT sequence correspond and/or are homologous to the part of the *E. coli* GFAT sequence extending between the β13 sheet and the β14 sheet, i.e. to the sequence extending approximately between amino acids 220 to 230 of *E. coli* GFAT.

Amino acids 340 to 370 of said human GFAT sequence correspond and/or are homologous to the part of the *E. coli* GFAT sequence extending between the β15 sheet and the α6 helix, i.e. to the sequence extending approximately between amino acids 235 to 250 of *E. coli* GFAT.

The invention relates in particular to a protein as defined above, in which the GFAT sequence corresponds to:

```
SEQ ID NO:2, corresponding to the human GFAT1
sequence,

SEQ ID NO:4, corresponding to the human GFAT2
sequence,

SEQ ID NO:6, corresponding to the human GFAT1 Alt
sequence.
```

The human GFAT1 sequence is in particular described in McKnight et al., *J. Biol. Chem.* (1992) 267:25208, and corresponds to the nucleotide sequence SEQ ID NO: 1.

The human GFAT2 sequence is in particular described in Oki et al., *Genomics* (1999) 57:227, and corresponds to the nucleotide sequence SEQ ID NO: 3.

The human GFAT1Alt sequence is in particular described in DeHaven et al., *Diabetes* (2001) 50:2419, and corresponds to the nucleotide sequence SEQ ID NO: 5.

The invention relates in particular to a protein as defined above, in which the purification tag sequence is inserted between two consecutive amino acids, said amino acids being included between amino acids:

```
43 to 47, 298 to 306, and/or 342 to 347 of SEQ ID
NO:2, 42 to 45, 299 to 307, and/or 343 to 348 of SEQ ID
NO:4

43 to 47, 316 to 324, and/or 360 to 365 of SEQ ID
NO:6
```

Amino acids 43 to 47 of SEQ ID NO: 2, 42 to 45 of SEQ ID NO: 4 and 43 to 47 of SEQ ID NO: 6 correspond, i.e. are homologous, to the part of the *E. coli* GFAT sequence extending between the β2 sheet and the β3 sheet, i.e. to the sequence extending approximately between amino acids 30 to 80 of *E. coli* GFAT.

Amino acids 298 to 306 of SEQ ID NO: 2, 299 to 307 of SEQ ID NO: 4 and 325 to 330 of SEQ ID NO: 6 correspond, i.e. are homologous, to the part of the *E. coli* GFAT sequence extending between the β13 sheet and the β14 sheet, i.e. to the sequence extending approximately between amino acids 220 to 230 of *E. coli* GFAT.

Amino acids 342 to 347 of SEQ ID NO: 2, 343 to 348 of SEQ ID NO: 4 and 360 to 365 of SEQ ID NO: 6 correspond, i.e. are homologous, to the part of the *E. coli* GFAT sequence extending between the β15 sheet and the α6 helix, i.e. to the sequence extending approximately between amino acids 235 to 250 of *E. coli* GFAT.

According to another particular embodiment, the invention relates more particularly to a protein as defined above, in which the purification tag sequence is inserted between two consecutive amino acids of the GFAT sequence, said amino acids being included in:

a part of the GFAT sequence corresponding and/or being homologous to the sequence extending approximately between amino acids 43 to 47 of human GFAT1, a part of the GFAT sequence corresponding and/or being homologous to the sequence extending approximately between amino acids 298 to 306, in particular 299 to 300, of human GFAT1, a part of the GFAT sequence corresponding and/or being homologous to the sequence extending approximately between amino acids 342 to 347 of the human GFAT1.

The invention relates more particularly to an above protein, in which the purification tag sequence is inserted between amino acids:

```
299 and 300 of SEQ ID NO:2, 300 and 301 of SEQ ID NO:4, 317 and 318 of SEQ ID NO:6.
```

The invention relates in particular to an above protein, in which the purification tag corresponds to a sequence of approximately 2 to approximately 10 amino acids, in particular of approximately 4 to approximately 8 amino acids.

Preferred purification tags according to the invention relate in particular to so-called FLAG tags (Sigma-Aldrich, France). These tags bind specifically to a given paratope, said paratope being able to belong to an antibody or to an antibody fragment for example. A particular example of a FLAG tag is constituted by the peptide sequence Asp-Tyr-Lys-Asp-Asp-Asp-Asp-Lys (SEQ ID NO: 18) for example.

Other preferred tags according to the invention are tags formed by several histidines. These tags can form complexes with divalent metallic cations such as $Ni^{2+}$ or $Co^{2+}$ for example.

The invention relates in particular to a protein as defined above, in which the purification tag is a hexa-histidine.

The sequence His-His-His-His-His-His (SEQ ID NO: 19) is designated hexa-histidine.

The invention relates more particularly to a protein as defined above corresponding to the sequences:

SEQ ID NO: 8, corresponding to the sequence SEQ ID NO: 2 in which a hexa-histidine is inserted between amino acids 299 and 300, SEQ ID NO: 10, corresponding to the sequence SEQ ID NO: 4 in which a hexa-histidine is inserted between amino acids 300 and 301, and SEQ ID NO: 12, corresponding to the sequence SEQ ID NO: 6 in which a hexa-histidine is inserted between amino acids 317 and 318.

The present invention also relates to a nucleic acid comprising or being constituted by a sequence coding for a protein as defined above.

The invention relates more particularly to a nucleic acid comprising or being constituted by the nucleotide sequence:

SEQ ID NO: 7 coding for the protein SEQ ID NO: 8, or

SEQ ID NO: 9 coding for the protein SEQ ID NO: 10, or

SEQ ID NO: 11 coding for the protein SEQ ID NO: 12, or by its complementary sequence, or being derived from said sequence by mutation, insertion or deletion of at least one nucleotide, provided that said nucleotide sequence codes for an enzymatically-active protein.

According to another embodiment, the present invention also relates to a eukaryotic or prokaryotic vector comprising a nucleic acid as defined above.

These vectors make it possible in particular to synthesize the proteins according to the invention in a eukaryotic or prokaryotic organism.

Advantageously the invention relates to a baculovirus-type expression vector allowing the synthesis of the proteins according to the invention in insect cells.

The present invention also relates to a process for the purification of a protein as defined above, from a solution comprising said protein, comprising a stage of bringing said solution into the presence of a compound binding specifically to the purification tag of said protein and a stage of separation of the complex formed by the binding of said protein to said compound from the other constituents of the solution.

The compound can be fixed to a solid support such that the complex formed between said compound and said protein can be recovered by centrifugation or filtration. Optionally said compound fixed on its support can be arranged in a column through which said solution is eluted.

Advantageously, the above process can also comprise a stage of dissociation of the complex formed by the binding of said protein to said compound in order to recover the purified protein.

The invention relates more particularly to a purification process as defined above, comprising a stage of bringing a solution comprising a protein as defined above into the presence of a compound comprising a divalent metallic cation such as $Ni^{2+}$ or $Co^{2+}$, in particular $Ni^{2+}$, and a stage of separation of the complex formed by the binding of the protein to said compound from the other constituents of the solution.

Advantageously, the above process can also comprise a stage of dissociation of the complex formed by the binding of said protein to said compound comprising a divalent metallic cation, in particular using imidazole, in order to recover the purified protein.

According to another embodiment the present invention relates to a process for the preservation of a protein as defined above in an enzymatically-active form, in particular at −80° C. or at 4° C., comprising the addition of said protein to a solution comprising:

approximately 1 mM to approximately 10 mM of fructose 6-phosphate, in particular approximately 1 mM, approximately 1 mM to approximately 5 mM of Tris(2-carboxyethyl)phosphine, in particular approximately 1 mM, approximately 5% to approximately 20% of glycerol, in particular approximately 10%.

The fructose-6-phosphate is a substrate of said protein.

Tris(2-carboxyethyl)phosphine is a reducing compound advantageously making it possible to maintain the property of resins carrying $Ni^{2+}$ or $Co^{2+}$ ions.

Advantageously the glycerol is a cryoprotective agent.

The present invention therefore also relates to a composition comprising an active GFAT protein, if appropriate, bound to a purification tag, such as a protein as defined above, said protein being capable of being preserved in an enzymatically-active form, for at least 8 days at a temperature of 2° C. to 10° C., in particular approximately 4° C., and for at least 12 months at a temperature of −100° C. to −20° C., in particular approximately −80° C., said protein being in combination with:

approximately 1 mM to approximately 10 mM of fructose 6-phosphate, in particular approximately 1 mM, approximately 1 mM to approximately 5 mM of Tris(2-carboxyethyl)phosphine, in particular approximately 1 mM, approximately 5% to approximately 20% of glycerol, in particular approximately 10%.

The present invention also relates to the use of a protein as defined above, for the screening of compounds modifying the activity of said protein, in particular for the screening of said protein inhibitor.

The activity of the proteins according to the invention can in particular be measured using the following methods:

the radiometric method described by Broschat et al., *Analytical Biochem.* (2002) 305:10-15, the so-called Nitro Blue Tetrazolium method described by Nakata et al., *J. Antibio.* (2001) 54:737-743.

the Morgan-Elson method described by Ghosh et al., *Method. Enzymol.* (1960) 5:414 and described in detail in the example which follows.

the APAD method described by Badet et al., *Biochemistry* (1987) 26:1940 and described in detail in the example which follows.

Advantageously these methods can be used for the screening, in particular at a high flow rate, of compounds modifying the activity of the proteins according to the invention.

The invention relates in particular to use as defined above, for the screening of compounds useful within the framework of the treatment or prevention of diabetes, in particular type II diabetes, obesity, acidosis, ketosis, arthritis, cancer, or osteoporosis.

BRIEF DESCRIPTION OF DRAWING FIGURE

Description of FIG. 1

FIG. 1 represents the plasmid pFastBac-gfat-His6 with a molecular weight of 6.89 kb. The cassette "Ampr" represents an ampicillin-resistance gene, the cassette "ori" represents a bacterial replication origin, the cassette "Gmr" represents a gentamicin-resistance gene, the cassette "Polh Pr" represents the polyhedrin promoter, the cassette gfat-his6 represents the gfat1 gene modified by the insertion of a sequence coding for a hexahistidine tag. The XbaI restriction sites in position 4.11 kb, and EcoRI in positions 4.56 kb and 6.60 kb are also represented.

DETAILED DESCRIPTION OF THE PREFERRED EMBODIMENTS

EXAMPLE 1

1. Synthesis and Cloning of the gfat1-His6 Gene

The EcoRI fragment of a cDNA corresponding to the human gfat1 gene was cloned in the EcoR I site of the pCRII vector (Invitrogen) in order to form the plasmid pCRII-gfat1. The nucleotide sequence of an internal purification tag composed of 6 histidine residues was introduced at position 898 of the gfat1 gene sequence cloned in pCRII by PCR with *Platinum pfx polymerase* (Roche) and the appropriate pair of primers:

```
Start Aat II-His6:
5' TGGACGTCTTTCTATCCATCGAATTAAACGAAC (SEQ ID NO:14)
TGCAGGACATCACCATCACCATCACGATCACCCCGG
ACG 3'

End Hinc II:
5' CAAAGTTGACTCTTCCTCTCATTGTGTTCACGA (SEQ ID NO:15)
CAGACTCTGGC 3'
``` according to the following protocol: 94° C., 2 minutes then 30 cycles (94° C. 45 seconds, 55° C. 1 minute, 72° C. 5 minutes) followed by 5 minutes' polymerization at 72° C. and returning to 4° C.

After digestion by AatII and HincII then purification on 1.5% Seaplaque agarose gel (Tebu), the amplicon (170 bp) was inserted at the level of the corresponding restriction sites into the pCRII-gfat1 construction. The 170 bp insert was introduced by ligation into the construction with a ratio of 3:1 at 16° C. overnight in the presence of T4 DNA ligase (Nebs). The ligation mixture (20 μl) thus obtained made it possible to transform a strain of E. coli JM109. Then, the XbaI-HindII fragment of the recombinant plasmid pCRII-gfat1-His6 was cloned in the donor plasmid pFastBac1 (Life Technologies Ltd). The plasmid pFastBac-gfat-His6 thus generated (FIG. 1) was verified by multiple digestions: SmaI, AccI/DraI, PstEI/XbaI, and by sequencing. With a view to improving the construction, the sequence upstream of the start codon was mutated at two positions by PCR, with the following pair of primers, in order to remove two open reading frames upstream of the gfat1 gene:

```
Start XbaI
5' AATCTAGATTCATGCTCGAGCGGCCGCCAGTGT (SEQ ID NO:16)
GATTGATATC 3'

End AfeI
5' ATTTTTATCAGAGCGCTGGGGGTGGCTATTGAC (SEQ ID NO:17)
AGG 3'
``` according to the protocol: 94° C. 2 minutes, then 30 cycles (94° C. 15 seconds, 55° C. 30 seconds, 68° C. 1 minute) followed by a 1 minute's polymerization at 68° C. and returning to 4° C.

The PCR fragment obtained, containing the two mutations, was purified on SeaPlaque gel (Tebu) at 0.7% then digested by XbaI and AfeI in order to replace its homologue in pFastBac-gfat-His6 in order to produce the donor plasmid pFastBac-gfat-His6-2orf to be used for transposition into the DH10Bac cells (Life Technologies Ltd). The construction was verified by SmaI, XbaI/PstEI, XbaI/HindIII digestions, and by sequencing.

A recombinant bacmid was isolated after transposition into the DH10Bac cells and used for transfecting Sf9 insect cells in the presence of Lipofectin (Life Technologies Ltd). The baculoviruses obtained were amplified in the Sf9 cells and the viral titre was measured at $5.10^7$ pfu/ml.

2. Production of the GFAT1-His6 Protein

Sf9 insect cells were cultured at 28° C. in the presence of SF900II medium (Life Technologies Ltd) in 5 l flasks under stirring at 100 rpm. The cells at a density of $2.10^9$ cells/l were infected by the recombinant baculovirus obtained above with an infection multiplicity of 2 (pfu/cell), then cultured for 72 hours.

The cells and the supernatant were separated by centrifugation (2500 g, 10 minutes at 4° C.). The cell pellets were washed in the presence of 20 mM Tris-HCl buffer, pH 7, centrifuged (4000 g, 45 minutes at 4° C.) and frozen at -80° C.

3. Purification of the GFAT1-His6 Protein

The cell pellet (20 g) was taken up in 50 ml of lysis buffer (50 mM $NaPO_4$, pH 7.5, 300 mM NaCl, 10 mM imidazole, 1 mM fructose-6-phosphate (fructose-6P), 1 mM TCEP (Tris (2-carboxyethyl)phosphine), 1 mM PMSF (phenylmethyl-sulphonyl fluoride), 10% glycerol and 1 protease inhibitor cocktail tablet without EDTA (Roche Applied Sciences) and subjected to grinding with a DynoMill at 4500 rpm (4 cycles of 30 seconds) in the presence of 40 g of microbeads 0.2 mm in diameter. The mixture was cooled down by circulation of ethylene glycol/water adjusted to -15° C. The crude extract obtained (100 ml, 445 mg of total proteins) was centrifuged at 4° C. for 20 minutes at 12000 rpm. The supernatant was subjected to ultracentrifugation at 4° C. (350,000 rpm, 1 hour). The supernatant thus obtained was mixed with 5 ml of 50% Ni-NTA matrix (Qiagen) for 2 hours at 4° C. The mixture was poured into an empty column then rinsed with 40 ml of washing buffer (50 mM $NaPO_4$, pH 7.5, 300 mM NaCl, 40 mM imidazole, 1 mM fructose-6P, 1 mM TCEP, 1 mM PMSF and one protease inhibitor cocktail tablet without EDTA (Roche Applied Sciences). Elution was carried out by successive stages with 125 and 500 mM imidazole in the same buffer as previously. 12 mg of functional GFAT1-His6 (protein assay according to Bradford's method) were thus obtained.

4. Preservation of the GFAT1-His6 Enzyme

The enzyme was then stored in 100 μl fractions in the presence of 1 mM fructose-6P, 1 mM TCEP and 10% glycerol at -80° C. The stability of the enzyme is several months at -80° C. and more than 8 days at 4° C.

5. Assay of the GFAT1-His6 Enzyme Activity

Different assay tests of the enzyme activity of GFAT1-His6 were used. These tests can be also used in order to screen compounds modifying, and in particular inhibiting, the activity of the GFAT1-His6. It is possible to easily adapt them to screening at a high flow rate.

Morgan-Elson Assay:

In this case the enzyme activity is monitored by a colorimetric test the principle of which is the following: the D-glucosamine-6P released by the enzyme is N-acetylated by acetic anhydride in alkaline medium (Ghosh et al., *Method. Enzymol.* (1962) 5:414), then the solution is treated with Ehrlich's reagent (para-dimethyl-amino-benzaldehyde, PDAB) in concentrated acid medium; the pink compound formed absorbs at 585 nm.

The enzymatic reaction takes place over 30 minutes at 37° C. in the presence of:

0.2 ml of 100 mM fructose-6P
0.25 ml of 60 mM L-Glutamine
0.25 ml of 150 mM $KPO_4$ buffer, pH 7
0.1 ml of 25 mM EDTA (ethylene diamine tetra-acetate), pH 7
up to 200 μl of sample (to be completed with $H_2O$ if necessary)

The reaction is stopped by immersion for 4 minutes in a water bath at 100° C. then centrifuged. 0.8 ml of the supernatant is sampled for assay of the glucosamine-6P according to the following protocol:

addition of 0.1 ml of saturated $NaHCO_3$,
addition of 0.1 ml of a 5% acetic anhydride solution in water prepared extemporaneously,
stirring and incubation for 5 minutes at ambient temperature,
incubation for 5 minutes in a bath at 100° C.,
addition of 0.2 ml of 0.8 M potassium borate, pH 9.1 (to be adjusted with 10 N KOH).
stirring and incubation for 7 minutes in a bath at 100° C.
addition of 3 ml of Ehrlich's reagent diluted 10 times in acetic acid, prepared extemporaneously, to the solution cooled down in ice,
incubation for 20 minutes at 37° C.

The activity of the GFAT was determined by comparison with a standard curve established using D-glucosamine as standard in a concentration range of 0 to 200 nmoles. The specific activity of the GFAT1-His6 obtained was thus measured at 1.7 U/mg. This is greater than the value of 0.4 U/mg obtained by Broschat et al., *J. Biol. Chem.* (2002) 277:14764, for the purification of a recombinant human GFAT1. This reflects a greater activity of the GFAT1-His6 and/or a greater purity of the enzyme preparation according to the invention.

The kinetic parameters of GFAT1-His6 have been characterized vis-à-vis glutamine ($K_m^{Gln}$=0.2 mM) and fructose-6P (F6P) ($K_m^{F6P}$=0.006 mM) by a spectrophotometric assay coupled with glutamate dehydrogenase according to the APAD test. This is in accordance with the values cited in the prior art ($K_m^{Gln}$=0.26 mM and $K_m^{F6P}$=0.007 mM for Broschat et al., *J. Biol. Chem.* (2002) 277:14764).

APAD Assay

This is an ultraviolet spectrophotometric assay of the GFAT activity. It is based on the continuous determination of the quantity of L-glutamate formed using GFAT and an analogue of NAD (nicotinamide adenine dinucleotide), APAD (3-acetylpyridine adenine dinucleotide), according to the following reaction (catalyzed by glutamate dehydrogenase (GDH)):

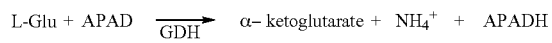

The measurement is carried out at 365 nm, at 37° C. Under these conditions an absorbance unit corresponds to 0.11 μmole of APADH formed.

The test comprises:

100 μl 3 mM APAD (2 mg/ml)

25 μl 2M KCl

100 μl of 1 M $KPO_4$ buffer, pH 7.2

100 μl of 100 mM Fructose-6P (30.41 mg/ml)

100 μl of 60 mM purified L-Glutamine (8.77 mg/ml)

$H_2O$ qsf 1 ml (taking into account the volumes to be added hereafter)

50 μl GDH sample to be assayed: 0.5 μg

It is also possible to use other assay processes, such as the radiometric assay described by Broschat et al., *Analytical Biochem.* (2002) 305:10-15 or the so-called Nitro Blue Tetrazolium assay described by Nakata et al., *J. Antibio.* (2001) 54:737-743.

---

The invention claimed is:

1. An isolated enzymatically-active protein possessing a glutamine:fructose-6-phosphate amidotransferase (GFAT) activity comprising:
   a GFAT sequence and at least one purification tag sequence, the purification tag sequence being inserted between two consecutive amino acids of the GFAT sequence corresponding to the sequences:
   SEQ ID NO: 8, consisting of a sequence SEQ ID NO: 2 in which a hexa-histidine is inserted between amino acids 299 and 300, or
   SEQ ID NO: 10, consisting of a sequence SEQ ID NO: 4 in which a hexa-histidine is inserted between amino acids 300 and 301, or
   SEQ ID NO: 12, consisting of a sequence SEQ ID NO: 6 in which a hexa-histidine is inserted between amino acids 317 and 318.

2. An isolated nucleic acid comprising or being constituted by the nucleotide sequence:
   SEQ ID NO: 7 coding for the protein SEQ ID NO: 8, or
   SEQ ID NO: 9 coding for the protein SEQ ID NO: 10, or
   SEQ ID NO: 11 coding for the protein SEQ ID NO: 12

3. A eukaryotic or prokaryotic vector comprising an isolated nucleic acid of claim 2.

4. A purification process for the isolated enzymatically-active protein possessing a GFAT activity of claim 1, from a solution comprising said protein, comprising a stage of bringing said solution into the presence of a compound binding specifically to the purification tag of said protein and a stage of separation of the complex formed by the binding of said protein to said compound from the other constituents of the solution.

5. The purification process of claim 4, comprising a stage of bringing a solution comprising a protein consisting of the sequences SEQ ID NO: 8, SEQ ID NO: 10 or SEQ ID NO: 12, into the presence of a compound comprising a divalent metallic caution such as $Ni^{2+}$ or $Co_{2+}$, in particular $Ni^{2+}$, and a stage of separation of the complex formed by the binding of the protein to said compound from the other constituents of the solution.

6. The purification process for the isolated enzymatically-active protein possessing a GEAT activity of claim 1, at −80° C. or at 4° C., comprising the addition of said protein to a solution comprising:
   1 mM to 10 mM of fructose 6-phosphate, or 1 mM,
   1 mM to 5 mM of Tris(2-carboxyethyl) phosphine, or 1 mM,
   5% to 20% of glycerol, or 10%.

7. A composition comprising the isolated enzymatically-active protein possessing a GFAT activity according to claim 1, said protein being capable of being preserved in an enzymatically-active form, for at least 8 days at a temperature of 20° C. to 10° C., in particular approximately 4° C., and for at least 12 months at a temperature of −100° C to 20° C., in particular approximately 80° C., said protein being in combination with:
   1 mM to 10 mM of fructose 6-phosphate, or 1 mM,
   1 mM to 5 mM of Tris(2-carboxyethyl) phosphine, or 1 mM,
   5% to 20% of glycerol, or 10%.

* * * * *

UNITED STATES PATENT AND TRADEMARK OFFICE
CERTIFICATE OF CORRECTION

PATENT NO.        : 7,625,734 B2                                          Page 1 of 1
APPLICATION NO.   : 10/563572
DATED             : December 1, 2009
INVENTOR(S)       : Badet-Denisot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 494 days.

Signed and Sealed this

Twenty-first Day of December, 2010

David J. Kappos
*Director of the United States Patent and Trademark Office*